(12) United States Patent
Lemoine

(10) Patent No.: US 8,118,837 B2
(45) Date of Patent: Feb. 21, 2012

(54) TAPERED-LOCK SPINAL ROD CONNECTORS AND METHODS FOR USE

(75) Inventor: Jeremy J. Lemoine, Austin, TX (US)

(73) Assignee: Zimmer Spine, Inc., Mineapolis, MN (US)

( * ) Notice: Subject to any disclaimer, the term of this patent is extended or adjusted under 35 U.S.C. 154(b) by 827 days.

(21) Appl. No.: 12/167,798

(22) Filed: Jul. 3, 2008

(65) Prior Publication Data

US 2010/0004686 A1 Jan. 7, 2010

(51) Int. Cl.
*A61B 17/70* (2006.01)
*A61B 17/04* (2006.01)

(52) U.S. Cl. ........ 606/246; 606/250; 606/264; 606/301; 606/305

(58) Field of Classification Search .......... 606/250–254, 606/301, 305, 308, 265, 246, 264, 151, 279, 606/103, 278, 324, 330, 326, 276, 277
See application file for complete search history.

(56) References Cited

U.S. PATENT DOCUMENTS

| | | | |
|---|---|---|---|
| 4,433,677 A | 2/1984 | Ulrich et al. | |
| 4,773,402 A | 9/1988 | Asher et al. | |
| 5,282,863 A | 2/1994 | Burton | |
| 5,549,608 A | 8/1996 | Errico et al. | |
| 5,683,392 A | 11/1997 | Richelsoph et al. | |
| 5,702,393 A | 12/1997 | Pfaifer | |
| 5,728,098 A | 3/1998 | Sherman et al. | |
| 5,954,725 A | 9/1999 | Sherman et al. | |
| 5,964,760 A | 10/1999 | Richelsoph | |
| 5,989,250 A | 11/1999 | Wagner et al. | |
| 5,997,539 A * | 12/1999 | Errico et al. | 606/278 |
| 6,132,430 A | 10/2000 | Wagner | |
| 6,132,434 A | 10/2000 | Shermann et al. | |
| 6,171,311 B1 | 1/2001 | Richelsoph | |
| 6,187,005 B1 | 2/2001 | Brace et al. | |
| 6,416,515 B1 | 7/2002 | Wagner | |
| 6,454,773 B1 | 9/2002 | Sherman et al. | |
| 6,485,491 B1 | 11/2002 | Farris et al. | |
| 6,562,040 B1 | 5/2003 | Wagner | |
| 6,565,566 B1 | 5/2003 | Wagner et al. | |

(Continued)

FOREIGN PATENT DOCUMENTS

WO WO 2008013539 A2 1/2008

OTHER PUBLICATIONS

Spinal Concepts, Inc., "The Bac-Fix—Posterior Lower Back Fixation System Written Surgical Technique," Aug. 1997, pp. 1-11.

(Continued)

*Primary Examiner* — Pedro Philogene
(74) *Attorney, Agent, or Firm* — Sprinkle IP Law Group

(57) ABSTRACT

A spine stabilization system having cylindrical bodies, plates, transverse members and resilient inserts for coupling a rod to bone fasteners. A first resilient insert may be positioned on a first rod. A cylindrical body, plate or transverse member may be positioned on the first resilient insert such that the first resilient insert is in a passage. A second resilient insert may be positioned on a second rod and positioned in the cylindrical body, plate or transverse member. The resilient inserts are advanced into the cylindrical body, plate or transverse member to lock the resilient inserts in place and couple the rods.

19 Claims, 8 Drawing Sheets

U.S. PATENT DOCUMENTS

| | | | |
|---|---|---|---|
| 6,565,567 B1 | 5/2003 | Haider | |
| 6,595,992 B1 * | 7/2003 | Wagner et al. | 606/250 |
| 6,613,050 B1 | 9/2003 | Wagner et al. | |
| 6,660,005 B2 | 12/2003 | Toyama et al. | |
| 6,783,528 B2 * | 8/2004 | Vincent-Prestigiacomo | 606/246 |
| 6,837,889 B2 | 1/2005 | Shluzas | |
| 6,843,791 B2 | 1/2005 | Serhan | |
| 6,866,664 B2 | 3/2005 | Schär et al. | |
| 6,918,911 B2 | 7/2005 | Biedermann et al. | |
| 7,022,122 B2 | 4/2006 | Amrein et al. | |
| 7,090,674 B2 | 8/2006 | Doubler et al. | |
| 7,104,993 B2 | 9/2006 | Baynham et al. | |
| 7,276,069 B2 | 10/2007 | Biedermann et al. | |
| 7,303,563 B2 | 12/2007 | Poyner et al. | |
| 7,320,555 B2 | 1/2008 | Chang et al. | |
| 7,322,982 B2 | 1/2008 | Vincent-Prestigiacomo | |
| 7,335,202 B2 | 2/2008 | Matthis et al. | |
| 7,445,627 B2 | 11/2008 | Hawkes et al. | |
| 7,585,299 B2 | 9/2009 | Rezach | |
| 7,585,314 B2 | 9/2009 | Taylor et al. | |
| 7,585,315 B2 | 9/2009 | Donath | |
| 7,678,112 B2 | 3/2010 | Rezach | |
| 7,678,139 B2 | 3/2010 | Garamszegi et al. | |
| 7,686,835 B2 | 3/2010 | Warnick | |
| 7,766,915 B2 | 8/2010 | Jackson | |
| 7,776,067 B2 | 8/2010 | Jackson | |
| 7,819,899 B2 | 10/2010 | Lancial | |
| 7,828,829 B2 | 11/2010 | Ensign | |
| 7,833,248 B2 | 11/2010 | Markworth et al. | |
| 7,862,594 B2 | 1/2011 | Abdelgany | |
| 7,892,259 B2 | 2/2011 | Biedermann et al. | |
| 7,892,263 B2 * | 2/2011 | Perez-Cruet et al. | 606/279 |
| 2002/0035366 A1 | 3/2002 | Walder et al. | |
| 2003/0028192 A1 | 2/2003 | Schar et al. | |
| 2003/0125742 A1 | 7/2003 | Yuan et al. | |
| 2004/0138660 A1 | 7/2004 | Serhan | |
| 2005/0027292 A1 | 2/2005 | Bernard et al. | |
| 2005/0080419 A1 | 4/2005 | Donath | |
| 2005/0085812 A1 | 4/2005 | Sherman et al. | |
| 2005/0096653 A1 | 5/2005 | Doubler et al. | |
| 2005/0096659 A1 | 5/2005 | Freudiger | |
| 2005/0154391 A1 | 7/2005 | Doherty et al. | |
| 2005/0177156 A1 | 8/2005 | Timm et al. | |
| 2005/0192573 A1 | 9/2005 | Abdelgany et al. | |
| 2005/0203515 A1 | 9/2005 | Doherty et al. | |
| 2005/0216003 A1 | 9/2005 | Biedermann et al. | |
| 2005/0240265 A1 | 10/2005 | Kuiper et al. | |
| 2005/0240266 A1 | 10/2005 | Kuiper et al. | |
| 2005/0261770 A1 | 11/2005 | Kuiper et al. | |
| 2005/0273099 A1 | 12/2005 | Baccelli et al. | |
| 2005/0277919 A1 | 12/2005 | Slivka et al. | |
| 2005/0277923 A1 | 12/2005 | Sweeney | |
| 2005/0277924 A1 | 12/2005 | Roychowdhury | |
| 2005/0277927 A1 | 12/2005 | Guenther et al. | |
| 2005/0277928 A1 | 12/2005 | Boschert | |
| 2005/0283157 A1 | 12/2005 | Coates et al. | |
| 2006/0025767 A1 | 2/2006 | Khalili | |
| 2006/0025768 A1 | 2/2006 | Iott et al. | |
| 2006/0036244 A1 | 2/2006 | Spitler et al. | |
| 2006/0079894 A1 | 4/2006 | Colleran et al. | |
| 2006/0089644 A1 | 4/2006 | Felix | |
| 2006/0149244 A1 | 7/2006 | Amrein et al. | |
| 2006/0155278 A1 | 7/2006 | Warnick | |
| 2006/0173454 A1 | 8/2006 | Spitler et al. | |
| 2006/0200128 A1 | 9/2006 | Mueller | |
| 2006/0200149 A1 | 9/2006 | Hoy et al. | |
| 2006/0229615 A1 | 10/2006 | Abdou | |
| 2006/0235393 A1 | 10/2006 | Bono et al. | |
| 2007/0043355 A1 | 2/2007 | Bette et al. | |
| 2007/0043357 A1 | 2/2007 | Kirschman | |
| 2007/0055235 A1 | 3/2007 | Janowski et al. | |
| 2007/0055242 A1 | 3/2007 | Bailly | |
| 2007/0093817 A1 | 4/2007 | Barrus et al. | |
| 2007/0093827 A1 | 4/2007 | Warnick | |
| 2007/0093831 A1 | 4/2007 | Abdelgany et al. | |
| 2007/0093833 A1 | 4/2007 | Kuiper et al. | |
| 2007/0100341 A1 | 5/2007 | Reglos et al. | |
| 2007/0123860 A1 | 5/2007 | Francis et al. | |
| 2007/0123862 A1 | 5/2007 | Warnick | |
| 2007/0123865 A1 | 5/2007 | Schlapfer et al. | |
| 2007/0123867 A1 | 5/2007 | Kirschman | |
| 2007/0162008 A1 | 7/2007 | Cline et al. | |
| 2007/0225707 A1 | 9/2007 | Wisnewski et al. | |
| 2007/0225708 A1 | 9/2007 | Biedermann et al. | |
| 2007/0225711 A1 | 9/2007 | Ensign | |
| 2007/0233080 A1 | 10/2007 | Na et al. | |
| 2007/0233087 A1 | 10/2007 | Schlapfer | |
| 2007/0260246 A1 | 11/2007 | Biedermann | |
| 2008/0004627 A1 | 1/2008 | Dalton | |
| 2008/0015579 A1 | 1/2008 | Whipple | |
| 2008/0027432 A1 | 1/2008 | Strauss et al. | |
| 2008/0045951 A1 | 2/2008 | Fanger et al. | |
| 2008/0045956 A1 | 2/2008 | Songer et al. | |
| 2008/0058809 A1 | 3/2008 | Graf | |
| 2008/0058812 A1 | 3/2008 | Zehnder | |
| 2008/0071277 A1 | 3/2008 | Warnick | |
| 2008/0082171 A1 | 4/2008 | Kuiper et al. | |
| 2008/0091200 A1 | 4/2008 | Kuiper et al. | |
| 2008/0091204 A1 | 4/2008 | Kuiper et al. | |
| 2008/0091205 A1 | 4/2008 | Kuiper et al. | |
| 2008/0154308 A1 | 6/2008 | Sherman et al. | |
| 2008/0161859 A1 | 7/2008 | Nilsson | |
| 2008/0161863 A1 | 7/2008 | Arnold et al. | |
| 2008/0183214 A1 | 7/2008 | Copp et al. | |
| 2008/0183216 A1 | 7/2008 | Jackson | |
| 2008/0195156 A1 | 8/2008 | Ainsworth et al. | |
| 2008/0234734 A1 | 9/2008 | Walder et al. | |
| 2008/0234757 A1 | 9/2008 | Jacofsky et al. | |
| 2008/0249570 A1 | 10/2008 | Carson et al. | |
| 2009/0005817 A1 | 1/2009 | Friedrich et al. | |
| 2009/0012567 A1 | 1/2009 | Biedermann et al. | |
| 2009/0069849 A1 | 3/2009 | Oh et al. | |
| 2009/0118767 A1 | 5/2009 | Hestad et al. | |
| 2010/0010544 A1 | 1/2010 | Fallin et al. | |
| 2010/0094344 A1 | 4/2010 | Trieu | |
| 2010/0094349 A1 | 4/2010 | Hammer et al. | |
| 2010/0114168 A1 | 5/2010 | Miller | |
| 2010/0114170 A1 | 5/2010 | Barrus et al. | |
| 2010/0174313 A1 | 7/2010 | Abdelgany et al. | |
| 2010/0234891 A1 | 9/2010 | Freeman et al. | |
| 2010/0249845 A1 | 9/2010 | Meunier et al. | |
| 2010/0298884 A1 | 11/2010 | Faizan et al. | |
| 2010/0312279 A1 | 12/2010 | Gephart et al. | |
| 2010/0312282 A1 | 12/2010 | Abdou | |
| 2010/0331886 A1 | 12/2010 | Fanger et al. | |
| 2010/0331887 A1 | 12/2010 | Jackson et al. | |
| 2011/0004245 A1 | 1/2011 | Wu et al. | |
| 2011/0077689 A1 | 3/2011 | Mickiewicz et al. | |

OTHER PUBLICATIONS http://www.newsrx.com/newsletter/Medical-Devices-and-Surgical-Technology-Week/2002-09-29/2002092933331QW.html.

Office Action issued in U.S. Appl. No. 12/174,484, mailed Apr. 15, 2011, 14 pages.

Office Action issued in U.S. Appl. No. 12/174,484, mailed Jun. 21, 2011, 14 pages.

* cited by examiner

TAPERED-LOCK SPINAL ROD CONNECTORS AND METHODS FOR USE

BACKGROUND

1. Field of the Disclosure

The present disclosure generally relates to spinal stabilization systems. More particularly, embodiments of the disclosure relate to spinal stabilization systems that may use cold-weld technology to couple rods to bone fasteners.

2. Description of Related Art

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

Spinal stabilization may involve accessing a portion of the spine through soft tissue. Spinal stabilization systems for a lumbar region of the spine may be inserted during a spinal stabilization procedure using a posterior spinal approach. Minimally invasive procedures and systems may reduce recovery time as well as trauma to the soft tissue surrounding a stabilization site.

SUMMARY

A spinal stabilization system may be installed in a patient to stabilize a portion of a spine. A spinal stabilization system may be installed using a minimally invasive procedure. An instrumentation kit may provide instruments and spinal stabilization system components necessary for forming a spinal stabilization system in a patient.

A spinal stabilization system may be used to achieve rigid pedicle fixation while minimizing the amount of damage to surrounding tissue. In some embodiments, a spinal stabilization system may be used to provide stability to two or more vertebrae. A spinal stabilization system may include a rod, two or more bone fastener assemblies, and/or a resilient insert. The bone fastener assembly may include, but is not limited to, a bone fastener and a body. A first portion of the bone fastener may couple to a portion of the spine during use. A first portion of a body may couple to a second portion of the bone fastener. A second portion of the body may couple to a rod during use. In some embodiments, an orientation of the bone fastener may be independent of the orientation of the body for a bone fastener assembly. After the bone fastener is placed in a vertebral body, the body coupled to the bone fastener may be positioned so that the rod can be positioned in the body and in at least one other body that is coupled to another vertebral body by a bone fastener.

Some embodiments disclosed herein provide an apparatus for joining two rods. The apparatus may include a first resilient insert, a second resilient insert, and a cylindrical collar. The first resilient insert may include a first set of two deflectable arms and a first channel formed between the first set of two deflectable arms. The channel may have a width approximately equal to the diameter of a first spinal rod. The second resilient insert may include a second set of two deflectable arms and a second channel formed between the second set of two deflectable arms. The channel may have a width approximately equal to the diameter of a second spinal rod. The first spinal rod and the second spinal rod may have a similar or dissimilar diameter or shape. The cylindrical body having a passage from a first end to a second end therein. The passage in the cylindrical body may have an inner diameter such that the first resilient insert has a width greater than the inner diameter of the cylindrical body when the first resilient insert is in a neutral state.

In some embodiments, advancement of the first resilient insert into the passage in the cylindrical body deflects the first set of two deflectable arms inward, causing the width of the first channel to decrease, and inhibiting the first resilient insert from moving relative to the cylindrical body. In some embodiments, the second resilient insert has a width greater than the inner diameter of the cylindrical body when the second resilient insert is in a neutral state. In some embodiments, advancement of the second resilient insert into the passage in the cylindrical body deflects the second set of two deflectable arms inward, causing the width of the second channel to decrease and inhibiting the second resilient insert from moving relative to the cylindrical body. In some embodiments, at least one of the first set of two deflectable arms and the second set of the two deflectable arms comprise beveled surfaces proximate the first channel or the second channel. In some embodiments, at least one of the first set of two deflectable arms and the second set of the two deflectable arms comprise radiused surfaces proximate the first channel or the second channel. In some embodiments, at least one of the first end and the second end of the cylindrical body comprises two recessed portions, such that each recessed portion has an associated width greater than the diameter of the rod. In some embodiments, the first channel in the first resilient insert comprises a first slot, such that compression of the first slot deflects the first set of two deflectable arms inward to decrease the width of the first channel. In some embodiments, the second channel in the second resilient insert comprises a second slot, such that compression of the second slot deflects the second set of two deflectable arms inward to decrease the width of the second channel. In some embodiments, at least one of the first resilient insert and the second resilient insert is cannulated. In some embodiments, at least one of the first set of two deflectable arms and the second set of two deflectable arms has a first width and a second width that is greater than the first width, such that advancement of the first resilient insert into the cylindrical body comprises advancement of the first resilient insert until the first width thereof contacts interior walls of the second end of the cylindrical body and the second width thereof is compressed against the interior walls of the second end of the cylindrical body, and such that advancement of the second resilient insert into the cylindrical body comprises advancement of the second resilient insert until the first width thereof contacts interior walls of the second end of the cylindrical body and the second width thereof is compressed against the interior walls of the second end of the cylindrical body.

Some embodiments disclosed herein provide a system for stabilizing a portion of a spine. In some embodiments, the system may include a first spinal rod, a second spinal rod and a spinal rod connector having a first resilient insert, a second resilient insert, and a cylindrical body. The first spinal rod may have a substantially circular cross-sectional geometry. The second spinal rod may have a substantially circular cross-sectional geometry. The first spinal rod and the second spinal rod may have similar or dissimilar diameter or shape. The spinal rod connector may include the first resilient insert, the second resilient insert and the cylindrical body. The first resilient insert may include a first set of two deflectable arms and a first channel formed between the first set of two deflectable arms. The second resilient insert may include a second set of two deflectable arms and a second channel formed between the second set of two deflectable arms. The cylindrical body may have a passage from a first end to a second end therein. The passage in the cylindrical body may have an inner diameter such that the first resilient insert has a width greater than the inner diameter of the cylindrical body when the first resilient insert is in a neutral state.

In some embodiments, advancement of the first resilient insert into the passage in the cylindrical body deflects the first set of two deflectable arms inward, causing the width of the first channel to decrease to inhibit movement of the resilient insert relative to the first spinal rod, and inhibiting the first resilient insert from moving relative to the cylindrical body. In some embodiments, the second resilient insert has a width greater than the inner diameter of the cylindrical body when the second resilient insert is in a neutral state.

In some embodiments, advancement of the second resilient insert into the passage in the cylindrical body deflects the second set of two deflectable arms inward, causing the width of the second channel to decrease to inhibit movement of the resilient insert relative to the second spinal rod and inhibiting the second resilient insert from moving relative to the cylindrical body. In some embodiments, at least one of the first set of two deflectable arms and the second set of the two deflectable arms comprise beveled surfaces proximate the first channel or the second channel.

In some embodiments, at least one of the first set of two deflectable arms and the second set of the two deflectable arms comprise radiused surfaces proximate the first channel or the second channel. In some embodiments, the second end of the cylindrical body comprises two recessed portions, such that each recessed portion has an associated width greater than the diameter of the rod. In some embodiments, the first channel in the first resilient insert comprises a first slot, such that compression of the first slot deflects the first set of two deflectable arms inward to decrease the width of the first channel. In some embodiments, the second channel in the second resilient insert comprises a second slot, such that compression of the second slot deflects the second set of two deflectable arms inward to decrease the width of the second channel. In some embodiments, the apparatus includes two or more bone fasteners. In some embodiments, each bone fastener has a threaded shank for advancement into a vertebral body and a head connected to the threaded shank, such that coupling the first spinal rod or the second spinal rod to the head inhibits motion of the vertebral body relative to the first spinal rod or the second spinal rod.

Some embodiments disclosed herein provide an apparatus for joining two rods. In some embodiments, the apparatus may include a first resilient insert, a second resilient insert and a plate. The first resilient insert may include a first set of two deflectable arms and a first channel formed between the first set of two deflectable arms, such that the channel has a width approximately equal to the diameter of a first spinal rod. The second resilient insert may include a second set of two deflectable arms and a second channel formed between the second set of two deflectable arms, such that the channel has a width approximately equal to the diameter of a second spinal rod. The first spinal rod and the second spinal rod may have similar or dissimilar diameter or shape. The plate may have a first surface and a second surface. The plate may have a first cavity formed a selected depth into the plate and having a first inner diameter for accommodating the first resilient insert. In some embodiments, the first resilient insert has a width greater than the inner diameter of the first cavity when the first resilient insert is in a neutral state.

In some embodiments, advancement of the first resilient insert into the first cavity deflects the first set of two deflectable arms inward, causing the width of the first channel to decrease, and inhibiting the first resilient insert from moving relative to the plate. The plate may have a second cavity formed a selected depth into the plate and having a second inner diameter for accommodating the second resilient insert. In some embodiments, the second resilient insert has a width greater than the inner diameter of the second cavity when the second resilient insert is in a neutral state. In some embodiments, advancement of the second resilient insert into the second cavity deflects the second set of two deflectable arms inward, causing the width of the second channel to decrease and inhibiting the second resilient insert from moving relative to the plate. In some embodiments, the first cavity and the second cavity are formed in the first surface. In some embodiments, the first cavity formed in the first surface of the plate includes a through hole to the second surface, such that a portion of the first resilient insert may be pulled through the through hole to advance the first resilient insert into the first cavity. In some embodiments, the second cavity formed in the first surface of the plate includes a through hole to the second surface such that a portion of the first resilient insert may be pulled through the through hole to advance the first resilient insert into the first cavity.

Some embodiments disclosed herein provide a system for stabilizing a portion of the spine. In some embodiments, the system includes a first spinal rod having a substantially circular cross-sectional geometry, a second spinal rod having a substantially circular cross-sectional geometry, a first resilient insert, a second resilient insert and a plate. In some embodiments, the first resilient insert includes a first set of two deflectable arms and a first channel formed between the first set of two deflectable arms, such that the channel has a width approximately equal to the diameter of the first spinal rod. In some embodiments, the second resilient insert includes a second set of two deflectable arms and a second channel formed between the second set of two deflectable arms, such that the channel has a width approximately equal to the diameter of the second spinal rod. The first spinal rod and the second spinal rod may have a similar or dissimilar diameter or shape. In some embodiments, the plate may have a first surface and a second surface. In some embodiments, the plate may have a first cavity and a second cavity formed therein. The first cavity may be formed a selected depth therein and may have a first inner diameter for accommodating the first resilient insert. The first resilient insert may have a width greater than the inner diameter of the first cavity when the first resilient insert is in a neutral state.

In some embodiments, advancement of the first resilient insert into the first cavity deflects the first set of two deflectable arms inward, causing the width of the first channel to decrease, and inhibiting the first resilient insert from moving relative to the plate. The second cavity may be formed a selected depth into the plate and have a second inner diameter for accommodating the second resilient insert.

In some embodiments, the second resilient insert has a width greater than the inner diameter of the second cavity when the second resilient insert is in a neutral state. In some embodiments, advancement of the second resilient insert into the second cavity deflects the second set of two deflectable arms inward, causing the width of the second channel to decrease and inhibiting the second resilient insert from moving relative to the plate. In some embodiments, the system includes two or more bone fasteners. In some embodiments, each bone fastener has a threaded shank for advancement into a vertebral body and a head connected to the threaded shank. In some embodiments, coupling the first spinal rod or the second spinal rod to the head inhibits motion of the vertebral body relative to the first spinal rod or the second spinal rod. In some embodiments, the first channel in the first resilient insert comprises a first slot such that compression of the first slot deflects the first set of two deflectable arms inward to decrease the width of the first channel. In some embodiments, the second channel in the second resilient insert comprises a second slot such that compression of the second slot deflects the second set of two deflectable arms inward to decrease the width of the second channel. In some embodiments, at least one of the first resilient insert and the second resilient insert is cannulated.

In some embodiments, at least one of the first set of two deflectable arms and the second set of two deflectable arms has a first width and a second width that is greater than the first width. In some embodiments, advancement of the first resilient insert into the cylindrical body comprises advancement of the first resilient insert until the first width thereof contacts interior walls of the second end of the cylindrical body and the second width thereof is compressed against the interior walls of the second end of the cylindrical body. In some embodiments, advancement of the second resilient insert into the cylindrical body comprises advancement of the second resilient insert until the first width thereof contacts interior walls of the second end of the cylindrical body and the second width thereof is compressed against the interior walls of the second end of the cylindrical body.

Some embodiments disclosed herein provide an apparatus for stabilizing a portion of a spine. The apparatus may include a first resilient insert, a second resilient insert, and a transverse member. The first resilient insert may have a first set of two deflectable arms and a first channel formed between the first set of two deflectable arms, wherein the channel has a width approximately equal to the diameter of a first spinal rod. The second resilient insert may have a second set of two deflectable arms and a second channel formed between the second set of two deflectable arms. The channel may have a width approximately equal to the diameter of a second spinal rod. The first spinal rod and the second spinal rod may have similar or dissimilar diameter or shape. The transverse member may have selected length. The transverse member may have a first end and a second end. The first end may have a first cavity formed a selected depth into the first end and having a first inner diameter for accommodating the first resilient insert. In some embodiments, the first resilient insert has a width greater than the inner diameter of the first cavity when the first resilient insert is in a neutral state.

In some embodiments, advancement of the first resilient insert into the first cavity deflects the first set of two deflectable arms inward, causing the width of the first channel to decrease, and inhibiting the first resilient insert from moving relative to the transverse member. The second end may include a second cavity formed a selected depth into the second end and having a second inner diameter for accommodating the second resilient insert.

In some embodiments, the second resilient insert has a width greater than the inner diameter of the second cavity when the second resilient insert is in a neutral state. In some embodiments, advancement of the second resilient insert into the second cavity deflects the second set of two deflectable arms inward, causing the width of the second channel to decrease and inhibiting the second resilient insert from moving relative to the transverse member. In some embodiments, the length of the transverse member is adjustable. In some embodiments, a central portion of the transverse member between the first cavity and the second cavity has a solid cross-section, and the central portion has an outer diameter less than the outer diameter of the transverse member near the first end or near the second end. In some embodiments, the first channel in the first resilient insert comprises a first slot such that compression of the first slot deflects the first set of two deflectable arms inward to decrease the width of the first channel. In some embodiments, the second channel in the second resilient insert comprises a second slot, such that compression of the second slot deflects the second set of two deflectable arms inward to decrease the width of the second channel. In some embodiments, at least one of the first resilient insert and the second resilient insert is cannulated. In some embodiments, at least one of the first set of two deflectable arms and the second set of two deflectable arms has a first width and a second width that is greater than the first width.

In some embodiments, advancement of the first resilient insert into the cylindrical body comprises advancement of the first resilient insert until the first width thereof contacts interior walls of the second end of the cylindrical body and the second width thereof is compressed against the interior walls of the second end of the cylindrical body. In some embodiments, advancement of the second resilient insert into the cylindrical body comprises advancement of the second resilient insert until the first width thereof contacts interior walls of the second end of the cylindrical body and the second width thereof is compressed against the interior walls of the second end of the cylindrical body.

Some embodiments disclosed herein provide a system for stabilizing a portion of a spine. The system may include a first spinal rod, a second spinal rod, and a cross-link apparatus. The first spinal rod may have a substantially circular cross-sectional geometry and be coupled to a first side of a portion of a spine. The second spinal rod may have a substantially circular cross-sectional geometry and be coupled to a second side of the portion of the spine. In some embodiments, the first spinal rod and the second spinal rod have similar or dissimilar diameter or shape. The cross-link apparatus may include a first resilient insert, a second resilient insert and a transverse member. The first resilient insert may include a first set of two deflectable arms and a first channel formed between the first set of two deflectable arms, wherein the channel has a width approximately equal to the diameter of a first spinal rod. The second resilient insert may include a second set of two deflectable arms and a second channel formed between the second set of two deflectable arms, wherein the channel has a width approximately equal to the diameter of a second spinal rod. The transverse member may include a first end and a second end. A first cavity may be formed a selected depth into the first end and having a first inner diameter for accommodating the first resilient insert. In some embodiments, the first resilient insert has a width greater than the inner diameter of the first cavity when the first resilient insert is in a neutral state.

In some embodiments, advancement of the first resilient insert into the first cavity deflects the first set of two deflectable arms inward, causing the width of the first channel to decrease, and inhibiting the first resilient insert from moving relative to the transverse member. The second end may comprise a second cavity formed a selected depth into the second end and having a second inner diameter for accommodating the second resilient insert. In some embodiments, the second resilient insert has a width greater than the inner diameter of the second cavity when the second resilient insert is in a neutral state.

In some embodiments, advancement of the second resilient insert into the second cavity deflects the second set of two deflectable arms inward, causing the width of the second channel to decrease and inhibiting the second resilient insert from moving relative to the transverse member.

In some embodiments, the system includes two or more bone fasteners, wherein each bone fastener has a threaded shank for advancement into a vertebral body and a head connected to the threaded shank. In some embodiments, coupling the first spinal rod or the second spinal rod to the head inhibits motion of the vertebral body relative to the first spinal rod or the second spinal rod. In some embodiments, a central portion of the transverse member between the first cavity and the second cavity has a solid cross-section and wherein the central portion has an outer diameter less than the outer diameter of the transverse member near the first end or the second end. In some embodiments, the first channel in the first resilient insert comprises a first slot, wherein compression of the first slot deflects the first set of two deflectable arms inward to decrease the width of the first channel. In some embodiments, the second channel in the second resilient insert comprises a second slot, wherein compression of the second slot deflects the second set of two deflectable arms inward to decrease the width of the second channel. In some embodiments, at least one of the first resilient insert and the second resilient insert is cannulated.

In some embodiments, at least one of the first set of two deflectable arms and the second set of two deflectable arms has a first width and a second width that is greater than the first width. In some embodiments, advancement of the first resilient insert into the cylindrical body comprises advancement of the first resilient insert until the first width thereof contacts interior walls of the second end of the cylindrical body and the second width thereof is compressed against the interior walls of the second end of the cylindrical body. In some embodiments, advancement of the second resilient insert into the cylindrical body comprises advancement of the second resilient insert until the first width thereof contacts interior walls of the second end of the cylindrical body and the second width thereof is compressed against the interior walls of the second end of the cylindrical body.

Other objects and advantages of the embodiments disclosed herein will be better appreciated and understood when considered in conjunction with the following description and the accompanying drawings.

BRIEF DESCRIPTION OF THE DRAWINGS

Advantages of the present disclosure will become apparent to those skilled in the art with the benefit of the following detailed description and upon reference to the accompanying drawings in which.

Figure 1:
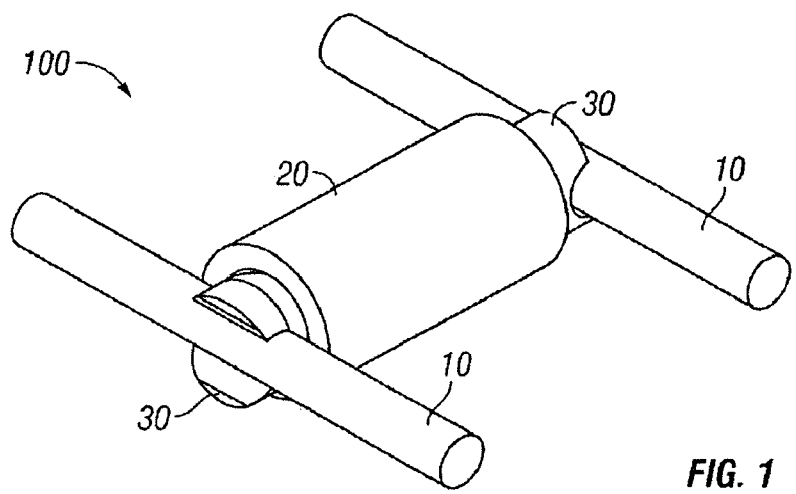
FIG. 1 depicts a perspective view of a portion of one embodiment of a spine stabilization system.

While the disclosure is susceptible to various modifications and alternative forms, specific embodiments thereof are shown by way of example in the drawings and will herein be described in detail. The drawings may not be to scale. It should be understood that the drawings and detailed description thereto are not intended to limit the disclosure to the particular form disclosed, but on the contrary, the intention is to cover all modifications, equivalents, and alternatives falling within the spirit and scope of the present disclosure as defined by the appended claims.

DETAILED DESCRIPTION

The disclosure and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments, are given by way of illustration only and not by way of limitation. Various substitutions, modifications, additions or rearrangements within the scope of the underlying inventive concept(s) will become apparent to those skilled in the art after reading this disclosure.

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited to only those elements but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

Different instruments may be used to form a spinal stabilization system in a patient using a minimally invasive procedure. The instruments may include, but are not limited to, positioning needles, guide wires, dilators, bone fastener driver, mallets, tissue wedges, tissue retractors, tissue dilators, bone awls, taps, and a rod length estimator. An instrumentation kit may include, but is not limited to, two or more detachable members (e.g., dilators), a tissue wedge, a rod positioner, an estimating tool, a seater, insert driver, and/or combinations thereof.

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spinal stabilization system. A minimally invasive procedure for stabilizing the spine may be performed without prior insertion of one or more spinal implants in some patients. In some patients, a minimally invasive procedure may be used to install a spinal stabilization system after one or more spinal implants are inserted using a posterior spinal approach.

A spinal stabilization system may be used to achieve rigid fixation while minimizing the amount of damage to surrounding tissue. In some embodiments, a spinal stabilization system may be used to provide stability to two adjacent vertebrae (i.e., one vertebral level). A spinal stabilization system may include two bone fastener assemblies. One bone fastener assembly may be positioned in each of the vertebrae to be stabilized. A rod may be coupled and secured to the bone fastener assemblies. As used herein, "coupled" components may directly contact each other or may be separated by one or more intervening members. In some embodiments, a single spinal stabilization system may be installed in a patient. Such a system may be referred to as a unilateral, single-level stabilization system or a single-level, two-point stabilization system. In some embodiments, two spinal stabilization systems may be installed in a patient on opposite sides of a spine. Such a system may be referred to as a bilateral, single-level stabilization system or a single-level, four-point stabilization system.

In some embodiments, a spinal stabilization system may provide stability to three or more vertebrae (i.e., two or more vertebral levels). In a two vertebral level spinal stabilization system, the spinal stabilization system may include three bone fastener assemblies. One bone fastener assembly may be positioned in each of the vertebrae to be stabilized. A rod may be coupled and secured to the three bone fastener assemblies. In some embodiments, a single two-level spinal stabilization system may be installed in a patient. Such a system may be referred to as a unilateral, two-level stabilization system or a two-level, three-point stabilization system. In some embodiments, two three-point spinal stabilization systems may be installed in a patient on opposite sides of a spine. Such a system may be referred to as a bilateral, two-level stabilization system or a two-level, six-point stabilization system.

In some embodiments, combination systems may be installed. For example, a two-point stabilization system may be installed on one side of a spine, and a three-point stabilization system may be installed on the opposite side of the spine. The composite system may be referred to a five-point stabilization system.

Minimally invasive procedures may reduce trauma to soft tissue surrounding vertebrae that are to be stabilized. Only a small opening may need to be made in a patient. For example, for a single-level stabilization procedure on one side of the spine, the surgical procedure may be performed through a 2 cm to 4 cm incision formed in the skin of the patient. In some embodiments, the incision may be above and substantially between the vertebrae to be stabilized. In some embodiments, the incision may be above and between the vertebrae to be stabilized. In some embodiments, the incision may be above and substantially halfway between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures. A minimally invasive procedure may reduce recovery time for the patient as compared to invasive spinal procedures.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system.

Cross-link devices allow transverse support of the spine in fusion procedures. More specifically, embodiments of the cross-link devices may limit or eliminate undesired motion (e.g., torsional movement, lateral bending) in a spinal fusion implant. In some applications, variable length cross-link devices may enable a surgeon to extend a fused portion of the spine to additional levels. In such cases, the surgeon may use extended rods, and use cross-link devices to provide selective support. The novel cross-link devices may provide several advantages over conventional devices, as persons of ordinary skill in the art who have the benefit of the description of the present disclosure will appreciate.

In some embodiments, spinal rods in a spine stabilization system may run parallel to each other and the spine. In some embodiments, spinal rods in a spine stabilization system may converge or diverge in a plane. In some embodiments, spinal rods in a spine stabilization system may reside in parallel planes but may otherwise be skewed. In some embodiments, it may be desirable to implant a spine stabilization system from a posterior approach. In some embodiments, it may be desirable to advance one or more components along a guide wire or other tool.

In some embodiments, multi-level spinal stabilization systems may involve stabilizing a cervical portion of the spine and a thoracic portion of the spine, or a thoracic portion of the spine and a lumbar portion of the spine. In some embodiments, multi-level spinal stabilization systems may involve spanning a junction between the cervical and thoracic portions of the spine. In some embodiments, multi-level spinal stabilization systems may involve spanning a junction between the thoracic and lumbar portions of the spine. Embodiments disclosed herein may couple spinal rods 10 that are contralaterally or ipsilaterally located on the spine. Embodiments disclosed herein may couple spinal rods that are parallel, skewed, or tangent to each other or a desired plane or axis.

FIG. 1 depicts one embodiment of connector 100 for joining two spinal rods 10. Connector 100 may be implanted using a minimally invasive surgical procedure. Connector 100 may include cylindrical body 20 and resilient inserts 30. Resilient inserts 30 may securely couple rods 10 to cylindrical body 20. In some embodiments, spinal rod connectors 100 such as depicted in FIG. 1 may be used in a single-level spinal stabilization system. In some embodiments, spinal rod connector 100 may be used in a multi-level spinal stabilization system.

Rods 10 may have shapes including, but not limited to, straight, bent, curved, s-shaped, and z-shaped. In some embodiments, rods 10 may have a substantially circular longitudinal cross section. In some embodiments, rods 10 may have other cross-sectional shapes including, but not limited to, regular shapes (oval, rectangular, rhomboidal, square) and irregular shapes. An instrumentation kit for a spinal stabilization system may include straight rods 10 and/or pre-shaped rods 10. Straight rods 10 and/or pre-shaped rods 10 may be contoured to accommodate patient anatomy if needed during the surgical procedure. Spinal rods 10 may have different thicknesses or diameters. In some embodiments, rods 10 may be smaller for the cervical portion of the spine, may be larger for thoracic portions of the spine, and may be even larger for lumbar portions of the spine. Embodiments disclosed herein may accommodate different sizes of rods 10. In some embodiments, connector 100 may connect a first rod 10 having a diameter sized for use in the cervical portion of the spine and a second rod 10 having a diameter sized for use in the thoracic portion of the spine. In some embodiments, connector 100 may connect a first rod 10 having a diameter sized for use in the thoracic portion of the spine and a second rod 10 having a diameter sized for use in the lumbar portion of the spine.

Figure 2A:
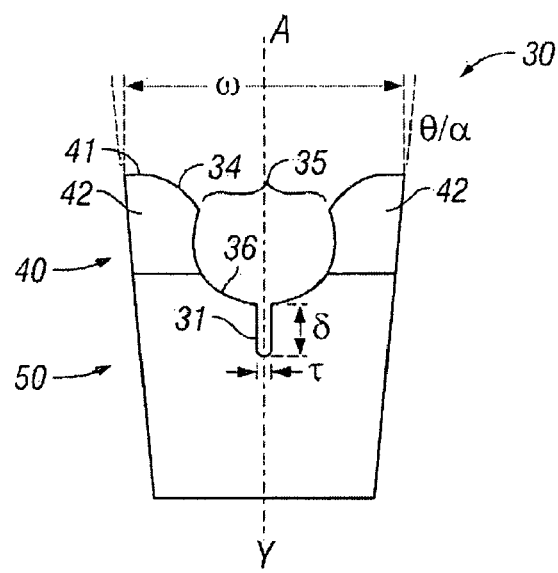
FIGS. 2A and 2B depict side views of embodiments of a resilient insert.
Figure 2B:
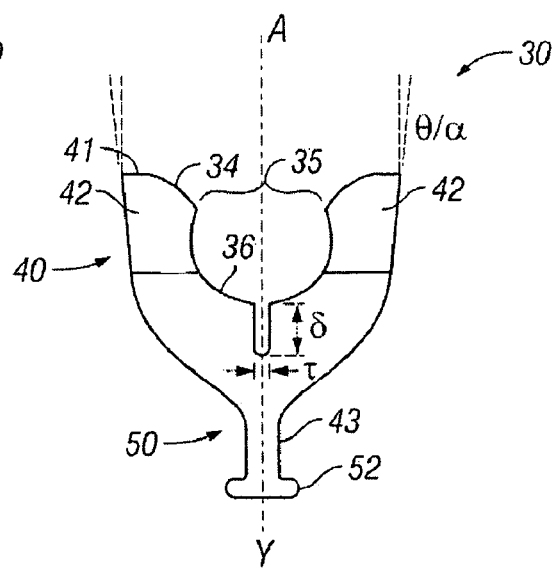

FIGS. 2A and 2B depict side views of embodiments of resilient insert 30 prior to insertion of resilient insert 30 into cylindrical body 20 of connector 100. In some embodiments, first end 40 of resilient insert 30 may have a set of opposing deflectable arms 42. In some embodiments, first end 40 may have an outer surface for contact with an inner surface of cylindrical body 20. Second end 50 may have a diameter less than the inner diameter of cylindrical body 20. In some embodiments, second end 50 may be formed into a neck having knob 52.

Resilient insert 30 may have channel 35 formed between deflectable arms 42 and have a geometric configuration to accommodate rod 10. In some embodiments, channel 35 of a first resilient insert 30 may a width approximately equal to the diameter of a first rod 10. In some embodiments, channel 35 of a second resilient insert 30 may have a width approximately equal to the diameter of a second rod 10.

Channel 35 may be formed with geometric configurations to include, but not limited to, a constant width, a variable width, an angular opening, a curved opening, a tapered opening, and combinations and/or portions thereof. The width of channel 35 may accommodate rod 10. In some embodiments, the width of channel 35 may be approximately the same width as the diameter of rod 10 having a circular cross-sectional geometry. In some embodiments, the width of channel 35 may be such that movement of rod 10 in resilient insert 30 may be resisted. In some embodiments, the width of channel 35 may be such that arms 42 provide little resistance to movement of rod 10 in resilient insert 30 when resilient insert 30 is in a neutral or undeflected state. The depth of channel 35 may accommodate all or a portion of the diameter of rod 10. In some embodiments, channel 35 may have curved surfaces to accommodate a diameter of rod 10. In some embodiments, channel 35 may have textured surfaces to accommodate a surface of rod 10. Inner surface 36 of channel 35 may be curved, angled, or some combination thereof to accommodate rod 10. In some embodiments, channel 35 may have inner surface 36 machined for selected contact with rod 10. Inner surface 36 may be grooved, textured, coated or otherwise machined for coupling resilient insert 30 to rod 10.

In some embodiments, the taper $\theta$ (Theta) associated with resilient insert 30 may be due to an increase in the thickness of the distal ends of deflectable arms 42. In some embodiments, the taper associated with resilient insert 30 may be due to the geometry of deflectable arms 42. Deflectable arms 42 may extend at some angle $\theta$ (Theta) relative to the longitudinal axis AY of resilient insert 30. In some embodiments, the taper of resilient insert 30 may be due to deflectable arms 42 being oriented at some angle $\theta$ (Theta) relative to the longitudinal axis of resilient insert 30. Each arm 42 may have an outer surface 40 that tapers some angle $\theta$ (Theta) relative to the longitudinal axis AY of resilient insert 30. When arms 42 are in a neutral state, the outward taper of arms 42 may allow channel 35 to have a width greater than the width of rod 10 positioned in channel 35. In some embodiments, deflection of arms 42 inward (i.e., angle $\theta$ (Theta) of deflectable arms 42 decreases) causes the taper of resilient insert 30 to decrease such that the width of channel 35 also decreases.

When arms 42 are deflected inward such that the taper $\theta$ (Theta) decreases, the width of channel 35 may decrease such that the width of channel 35 is substantially the same as the diameter of rod 10 positioned in channel 35. When the width of channel 35 is substantially equal to the width or diameter of rod 10, rod 10 may be inhibited from moving relative to resilient insert 30. In some embodiments, rod 10 may be captured by resilient insert 30 when the taper is less than 5 degrees. In some embodiments, rod 10 may be captured by resilient insert 30 when the taper is less than 10 degrees.

In some embodiments, channel 35 may include slot 31 having thickness $\tau$ (tau) and depth $\delta$ (delta). In some embodiments, closing slot 31 may decrease the width of channel 35 such that the width is substantially equal to the diameter of rod 10 positioned in channel 35. As used herein, the term "closing" generally refers to decreasing the opening of slot 31 using compression, torsion, or some combination to decrease the distance between arms 42. Thus, closing slot 31 may result in the sides of slot 31 touching or not touching at any point in slot 31. Closing slot 31 may also affect the taper of resilient insert 30. In some embodiments, the change in the taper of resilient insert 30 may be due solely to the closure or partial closure of slot 31. In some embodiments, the taper may be changed by a combination of deflecting deflectable arms 42 and closing or partially closing slot 31.

Still referring to FIGS. 2A and 2B, in some embodiments, resilient insert 30 may have surfaces 41 and 34. Surfaces 41 or 34 may be beveled or radiused to facilitate insertion of rod 10 into channel 35. In some embodiments, beveled or radiused surfaces 41 or 34 may facilitate positioning of rod 10 in resilient insert 30, which may be useful during Minimally Invasive Surgery (MIS). In some embodiments, beveled or radiused surfaces 41 or 34 may provide more visibility during surgery, which may allow a surgeon to verify the procedure. In some embodiments, beveled or radiused surfaces 41 or 34 may serve as a guide for rods 10. During MIS procedures, surface 41 or 34 may contact rod during positioning of resilient insert 30 on rod 10. A surgeon may apply pressure to rod 10 in contact with surface 41 or 34. Surface 41 or 34 may guide resilient insert 30 onto rod 10 such that the surgeon does not need to visualize the connection.

In some embodiments, channel 35 of resilient insert 30 may have a width to accommodate various sizes of rods 10. In some embodiments, a set of resilient inserts 30 may include sizes for various rods 10. A set of resilient inserts 30 may include resilient inserts 30 for rods 10 having a diameter of 4 mm, resilient inserts 30 for rods having a diameter of 5 mm, resilient inserts 30 for rods having a diameter of 6 mm, and resilient inserts 30 for rods having a diameter of 7 mm. In some embodiments, resilient inserts 30 may be sized to accommodate a range of diameters of rods 10. Resilient insert 30 may be sized to accommodate rods 10 having a diameter between 3-5 mm and a second resilient insert 30 sized to accommodate rods 10 having a diameter between 5-7 mm. In some embodiments, surface 36 of channel 35 may be textured or smoothed for contact with rod 10. In some embodiments, each resilient insert 30 provided in an instrumentation set may have substantially the same outer diameter.

Resilient insert 30 may be rotatably positioned in cylindrical body 20 such that resilient insert 30 is able to move radially and/or rotationally relative to cylindrical body 20 (or cylindrical body 20 relative to first resilient insert 30) within a defined range of motion. A range of motion may be provided within a plane, such as by first resilient insert 30 allowing rotation of rod 10 within channel 35. Resilient insert 30 may be rotatably positioned in cylindrical body 20 such that resilient insert 30 is able to move radially and/or rotationally relative to cylindrical body 20 (or cylindrical body 20 relative to resilient insert 30) within a defined range of motion.

Figure 3A:
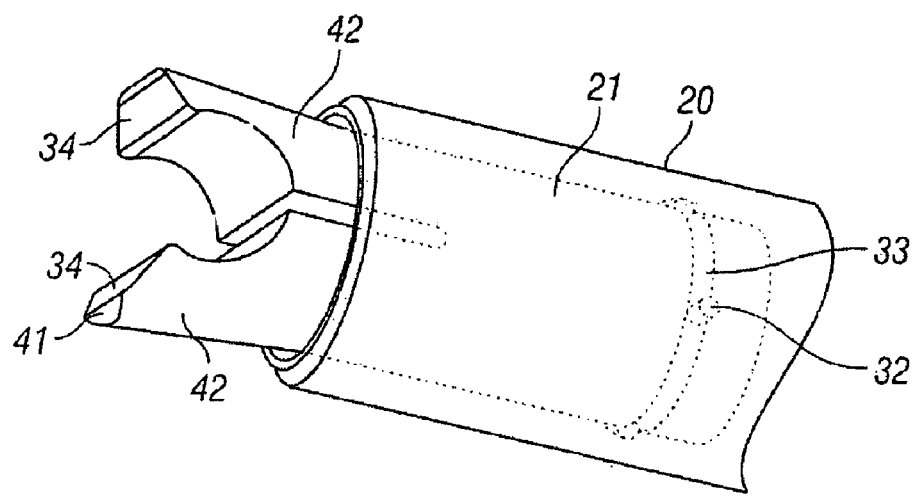
FIGS. 3A and 3B depict perspective views of embodiments of a connector.
Figure 3B:
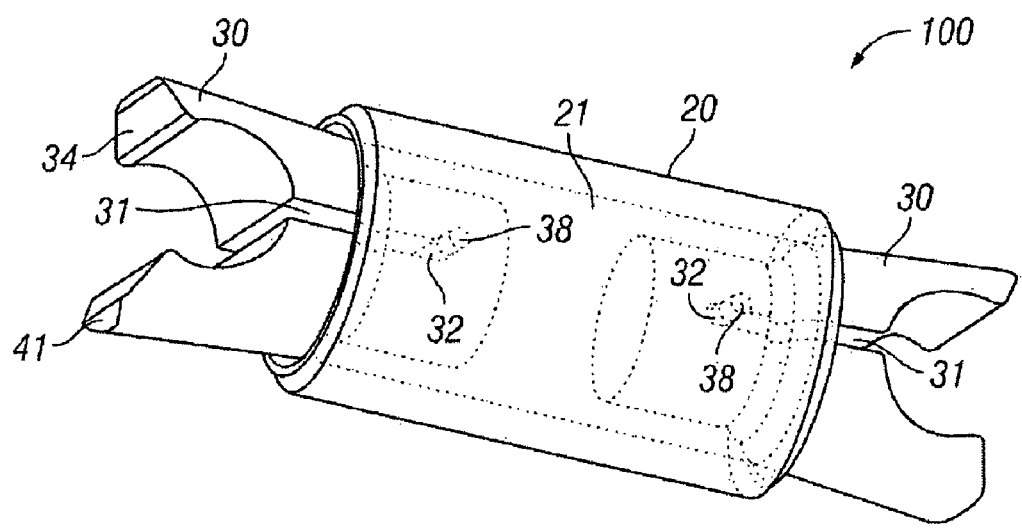

In some embodiments, resilient insert 30 may be positioned in cylindrical body 20 for receiving rod 10. FIGS. 3A and 3B depict perspective views of embodiments of cylindrical body 20 with resilient insert 30 inserted in at least one end. Rod 10 may be inserted in resilient insert 30 and resilient insert 30 may be advanced into cylindrical body 20 to capture rod 10 (see FIGS. 4A-4C). In some embodiments, resilient insert 30 may include pin 32. In some embodiments, pin 32 may retain resilient insert 30 in cylindrical body 20. Pin 32 may allow pre-positioning resilient insert 30 in cylindrical body 20.

Cylindrical body 20 may include passage 21 from a first end to a second end. In some embodiments, passage 21 may include groove 33 around a portion thereof. In some embodiments, resilient insert 30 may include pin 32. In some embodiments, when resilient insert 30 is advanced into passage 21, pin 32 may seat in groove 34. In some embodiments, groove 33 may be positioned such that when pin 32 is seated in groove 33, a portion of resilient insert 30 extends from cylindrical body 20. In some embodiments, when pin 32 is seated in groove 33, deflectable arms 42 extend from cylindrical body 20 in an undeflected or neutral state. In some embodiments, when pin 32 is seated in groove 33, deflectable arms 42 extend from cylindrical body 20 in a partially deflected state. Deflectable arms 42 in a partially deflected state may provisionally lock rod 10 in resilient insert 30. Deflectable arms 42 in a deflected state may narrow the width of channel 35 to resist rod 10 from withdrawing from channel 35. A surgeon may provisionally lock rod 10 in resilient insert 30 in a first cylindrical body 20 and then move rod 10 caudal or cephalad to adjust the spine, or the surgeon may provisionally lock rod 10 in a first cylindrical body 20 and then position rod 10 in other cylindrical body 20 positioned on the spine.

In some embodiments, arms 42 may include flanges for engagement with various tools. In some embodiments, flanges may be engaged by a tool. By pulling on flange while pushing on rod 10, rod 10 may be advanced into resilient insert 30. Embodiments disclosed herein may not require torque to insert rod 10 into resilient inserts 30. During implantation, rod 10 or resilient insert 30 may be exposed to only compressive or tensile forces. By pushing down on resilient insert 30 and pulling on flange or cylindrical body 20, resilient insert 30 may be advanced into cylindrical body 20. Flanges may provide sufficient support for the tensile and compressive forces used to position resilient insert 30 in cylindrical body 20 without applying torques to resilient insert 30 or cylindrical body 20. If the surgeon needs to remove or withdraw resilient insert 30 from cylindrical body 20, a tool may engage flanges. By pushing on cylindrical body 20 or flanges and pulling on resilient insert 30, resilient insert 30 may be removed without applying torques to resilient insert 30 or cylindrical body 20.

FIG. 3B depicts a perspective view of one embodiment of connector 100. Resilient inserts 30 may be inserted and advanced into passage 21 in cylindrical body 20. Pin 32 may be inserted in opening 38 and through slot 31 to secure resilient insert 30 in cylindrical body 20. In some embodiments, opening 38 is positioned such that pin 32 advanced through opening 38 may retain resilient insert 30 in a neutral state. Thus, resilient insert 30 may be prevented from withdrawing from cylindrical body 20, but may be advanced into cylindrical body 20 to securely couple rod 10 to cylindrical body 20. In some embodiments, opening 38 may be positioned such that pin 32 positioned in opening 38 retains resilient insert 30 in a semi-deflected state. Thus, resilient insert 30 may be prevented from withdrawing from cylindrical body 20 and rod 10 may be provisionally retained in resilient insert 30 to provisionally lock rod 10 to cylindrical body 20. In some embodiments, opening 38 may be positioned such that pin 32 positioned in opening 38 retains resilient insert 30 in a deflected state. Thus, resilient insert 30 may be prevented from withdrawing from cylindrical body 20 and rod 10 may be securely retained in resilient insert 30 to couple rod 10 to cylindrical body 20.

Figure 4A:
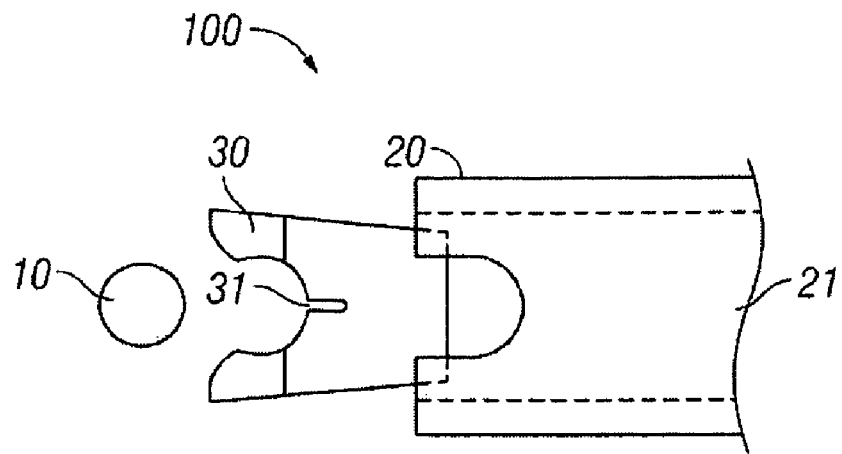
FIGS. 4A-4C depict side views of embodiments of a connector, illustrating one method for securing a rod to the connector.
Figure 4B:
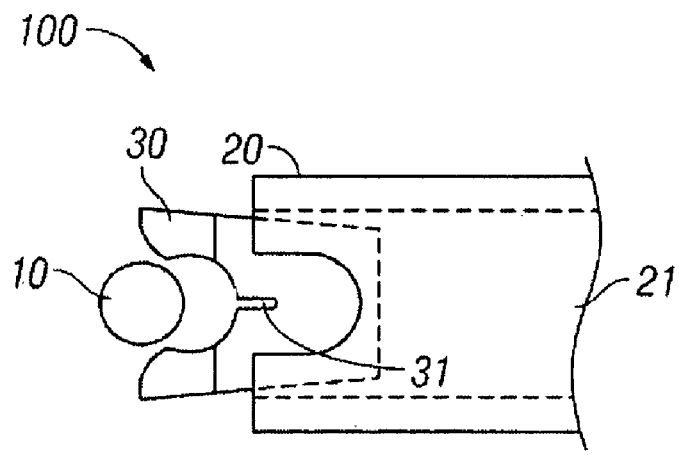
Figure 4C:
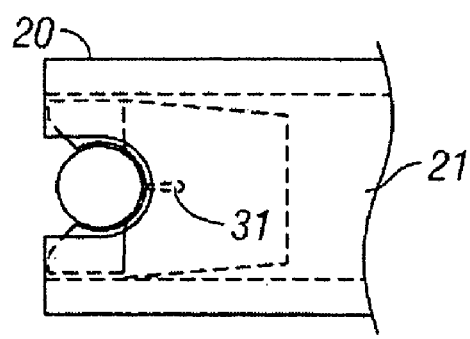

Rod 10 may be positioned in resilient insert 30 and resilient insert 30 may be advanced into cylindrical body 20 to couple rod 10 to cylindrical body 20. FIGS. 4A-4C depict side views of rod 10, a portion of cylindrical body 20, and resilient insert 30. FIGS. 4A-4C may depict steps in the assembly of connector 100. FIG. 4A depicts a side view of rod 10, resilient insert 30 and cylindrical body 20 prior to insertion of rod 10 into resilient insert 30 and before insertion of resilient insert 30 into cylindrical body 20. FIG. 4B depicts a side view of rod 10, resilient insert 30 and cylindrical body 20 during insertion of rod 10 or resilient insert 30. In some embodiments, rod 10 may be inserted into resilient insert 30 before resilient insert 30 is inserted into cylindrical body 20. In some embodiments, rod 10 may be inserted into resilient insert 30 after resilient insert 30 is inserted into cylindrical body 20. In some embodiments, rod 10 may be inserted into resilient insert 30 at the same time as resilient insert 30 is inserted into cylindrical body 20. FIG. 4C depicts a side view of rod 10, resilient insert 30 and cylindrical body 20 after insertion of rod 10 into resilient insert 30 and after advancement of resilient insert 30 into cylindrical body 20.

Figure 5A:
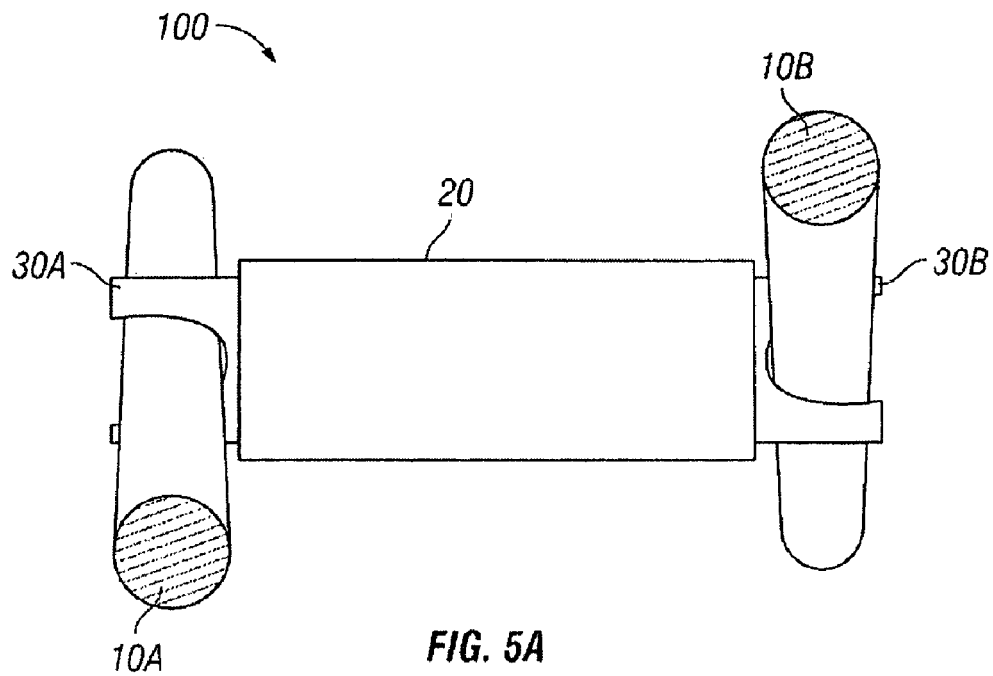
FIGS. 5A-5B depict side views of one embodiment of a connector coupled to two rods.
Figure 5B:
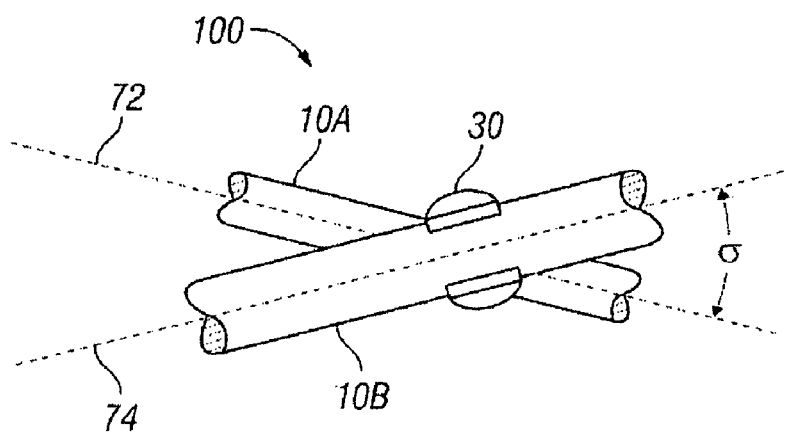

Some embodiments of connector 100 may couple rods 10 that are misaligned or otherwise not parallel. FIGS. 5A and 5B depict side and end views of one embodiment of connector 100 in which first resilient insert 30A is inserted in cylindrical body at some angle relative to second resilient insert 30B. In FIG. 5A, rods 10A and 10B are depicted as lying at two different angles in two substantially parallel planes. In some embodiments, resilient inserts 30A and 30B may be rotated in cylindrical body 20 to accommodate rods 10A and 10B that are skewed relative to each other. In FIG. 5B, rods 10A and 10B are depicted at an angle σ (Sigma). In some embodiments, rod 10A inserted in resilient insert 30A may be rotated some angle relative to rod 10B inserted in resilient insert 30B such that longitudinal axis 72 of rod 10A is maintained at a selected angle σ (Sigma) relative to longitudinal axis 74 of rod 10B. A range of motion of rod 10 may be provided by first resilient insert 30A at a first angle and second resilient insert 30B at a second angle. In some embodiments, a first resilient insert 30A may be constrained by pin 32, such as depicted in FIG. 3B. In some embodiments, a second resilient insert 30B may be constrained by pin 32, such as depicted in FIG. 3A. Thus, embodiments disclosed herein may include resilient inserts 30 with pins 32 positioned in grooves 33 or openings 38 to provide a range of motion of resilient insert 30 in cylindrical body 20 prior to advancing resilient insert 30 in cylindrical body 20.

Figure 6:
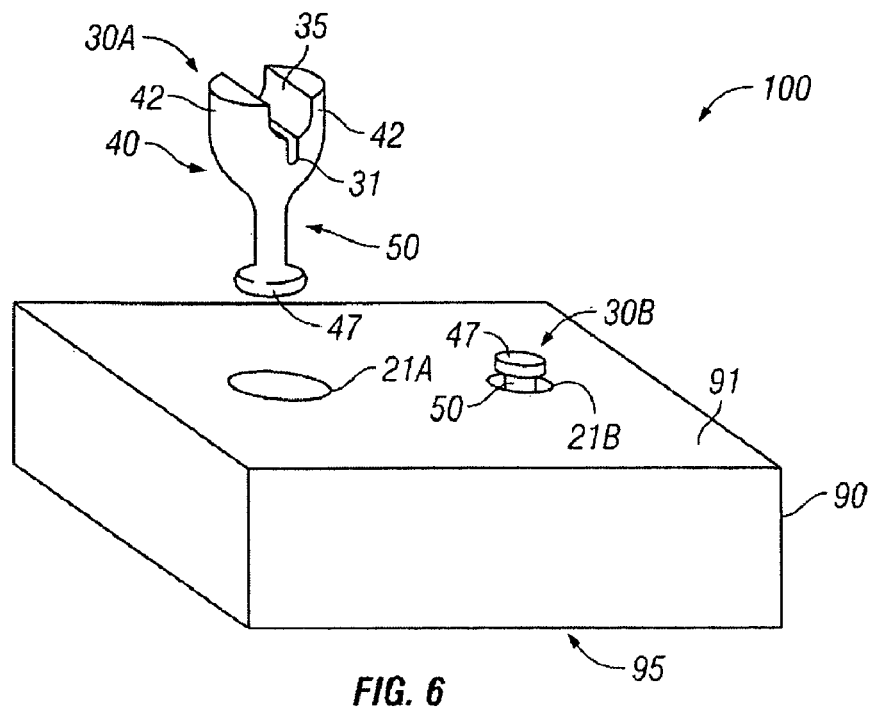
FIG. 6 depicts a perspective and side exploded view of one embodiment of a portion of a spine stabilization system.

Some embodiments of connectors 100 may utilize plate 90 for coupling rods 10. FIG. 6 depicts a perspective view of one embodiment of connector 100 comprising plate 90 and resilient inserts 30A and 30B. Plate 90 may be curved to accommodate a portion of the spine or may be flat. Plate may have an angular profile, such as depicted in FIG. 6, or may have beveled or radiused edges. In some embodiments, the overall shape of plate 90 may be rectangular (as shown), or may be oval, circular, or some other shape. In some embodiments, plate 90 may have first surface 91 and second surface 95. In some embodiments, resilient inserts 30A and 30B advanced into plate 90 may form connector 100. In some embodiments, passage 21A formed in plate 90 may have a large opening on first side 91 and a small opening on second side 95. In some embodiments, passage 21B formed in plate 90 may have a small opening on first side 91 and a large opening on second side 95.

In some embodiments, resilient inserts 30A or 30B may be advanced into plate 90 by compression. In some embodiments, resilient inserts 30A or 30B may be advanced into plate 90 by tension. Resilient inserts 30A or 30B may couple rods 10 to plate 90 but may allow some degree of freedom for rod 10. In some embodiments, plate 90 may constrain rods 10 to a single plane but may allow rods 10 to diverge or converge. In some embodiments, plate 90 may connect rods 10 located ipsilaterally. Channels 35 of resilient inserts 30A and 30B may be substantially aligned. In some embodiments, plate 90 may connect rods 10 located contralaterally. Channels 35 of resilient inserts 30A and 30B may be substantially parallel.

In some embodiments, resilient insert 30A or 30B, such as depicted in FIG. 2B, may be inserted into passage 21A or 21B in plate 90. In some embodiments, resilient insert 30A or 30B may rotate about the longitudinal axis of resilient insert 30A or 30B when resilient insert 30A or 30B is positioned in passage 21A or 21B. Rod 10 may be positioned in channel 35. Resilient insert 30A or 30B may be advanced into passage 21A or 21B in plate 90. Rod 10 may be securely coupled to plate 90 when resilient insert 30A or 30B is advanced into plate 90. In some embodiments, resilient insert 30A or 30B may be inserted in passage 21A via a larger opening in first surface 91 of plate 90. In some embodiments, resilient insert 30 may be inserted in passage 21B via a larger opening in second surface 95 of plate 90. FIG. 6 depicts resilient insert 30A prior to insertion of resilient insert 30 into plate 90 of connector 100. In some embodiments, resilient insert 30A or 30B may have a first end 40 having a set of opposing deflectable arms 42 and a second end 50 having a neck 43 and knob 52. Second end 50 of resilient insert 30A may be inserted into passage 21A on first surface 91 of plate 90 such that a portion of second end 50 of resilient insert 30A extends through plate 90 and out second surface 95. In some embodiments, a portion of second end 50 includes knob 47. In some embodiments, second end 50 includes knob 47 and shank 43. Pulling shank 43 and/or knob 47 may advance first end 40 of resilient insert 30A into passage 21A. Deflectable arms 42 may contact inner surface of passage 21A and deflect inward to narrow the width of channel 35.

In some embodiments, rod 10 may be positioned in channel 35 of resilient insert 30A or 30B and resilient insert 30A or 30B may be advanced into plate 90. In some embodiments, resilient insert 30A or 30B may be positioned in passage 21A or 21B in plate 90 before rod 10 is positioned in resilient insert 30A or 30B. In some embodiments, resilient insert 30 may be positioned in passage 21A or 21B and rotated before advancement into passage 21A or 21B.

In some embodiments, resilient insert 30 may be advanced into passage 21A or 21B using compression. In some embodiments, pushing on rod 10 positioned in channel 35 may advance resilient insert 30 into passage 21A or 21B in plate 90. In some embodiments, pushing on surfaces 33 of resilient insert 30 may advance resilient insert 30 into passage 21A or 21B. In some embodiments, resilient inserts 30 may be advanced into passage 21A or 21B using tension. In some embodiments, resilient inserts 30 may be advanced into passage 21A or 21B by pulling knob 47 of resilient insert 30. Rod 10 may be positioned in channel 35 of resilient insert 30. Resilient insert 30 may be positioned in passage 21A on first surface 91 such that second end 50 extends through plate 90 and is accessible by a tool. In some embodiments, the tool may pull on second end 50 to advance resilient insert 30 into plate 90. In some embodiments, the tool may pull on knob 47 to advance resilient insert 30 into plate 90.

Figure 7:
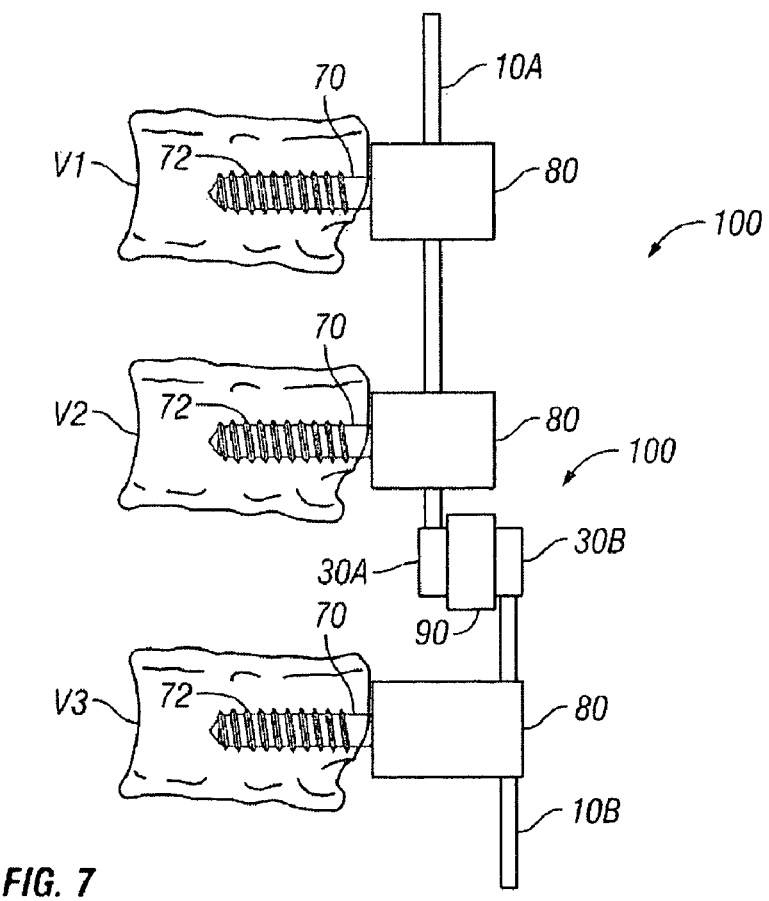
FIG. 7 depicts a perspective view of one embodiment of a connector.

FIG. 7 depicts a sagittal view of one embodiment of connector 100. In some embodiments, bone fasteners 72 may be advanced into vertebrae V1, V2 and V3. Collars 80 may be coupled to each of bone fasteners 72. Rods 10A and 10B may couple two or more collars. In FIG. 7, plate 90 is positioned between vertebrae V2 and V3 to connect rods 10A and 10B. First rod 10A may be positioned in first resilient insert 30A of connector 100. Second rod 10B may be positioned in second resilient insert 30B of connector 100. First resilient insert 30A may be advanced into plate 90 to couple rod 10A to plate 90. Second resilient insert 30B may be advanced into plate 90 to couple rod 10B to plate 90. Connector 100 formed from plate 90 and resilient inserts 30A and 30B may be used to couple two rods 10A and 10B to span a junction, provide additional rigidity to a spine stabilization system, and the like. In FIG. 7, first resilient insert 30A and second resilient insert 30B are depicted on opposite sides of plate 90, and connector 100 is disposed generally between rods 10A and 10B. However, first resilient insert 30A and second resilient insert 30B may be advanced into plate 90 on the same surface (i.e., first surface 91 or second surface 95), and plate 90 may be positioned anterior or posterior to rods 10A or 10B.

Figure 8A:
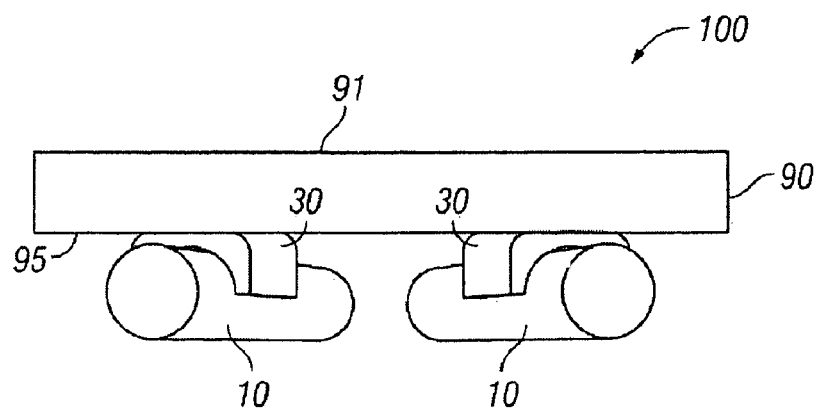
FIGS. 8A and 8B depict end and posterior views of one embodiment of a portion of a spine stabilization system.
Figure 8B:
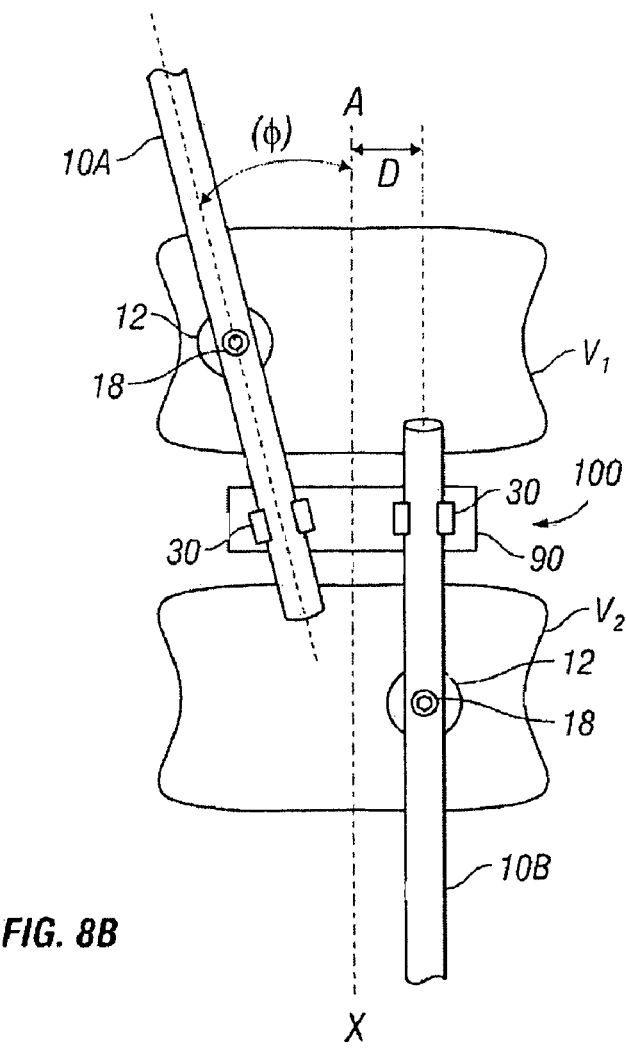

FIG. 8A depicts a side view of one embodiment of connector 100 having plate 90 with resilient inserts 30. FIG. 8B depicts a posterior view of a portion of a spine having one embodiment of connector 100. In FIG. 8B, first rod 10A is connected to a first vertebra V1 with bone fastener assembly 12 and oriented at some angle rho1 relative to the axis AX of the spine. Second rod 10B is shown connected to a second vertebra V2 with bone fastener assembly 12 and oriented substantially parallel with the axis AX of the spine. Plate 90 may be positioned anterior to rod 10A and/or rod 10B (as shown) or may be positioned posterior to rod 10A and/or rod 10B. In some embodiments, plate 90 may be positioned to connect two rods located ipsilaterally. In some embodiments, plate 90 may be positioned to connect two rods located contralaterally. Resilient inserts 30 may be positioned in 21A and 21B and rods 10A and 10B may be positioned in channels 35. Resilient inserts 30 may be advanced into passages 21A and 21B in plate 90 to couple rods 10A and 10B to plate 90.

Figure 9A:
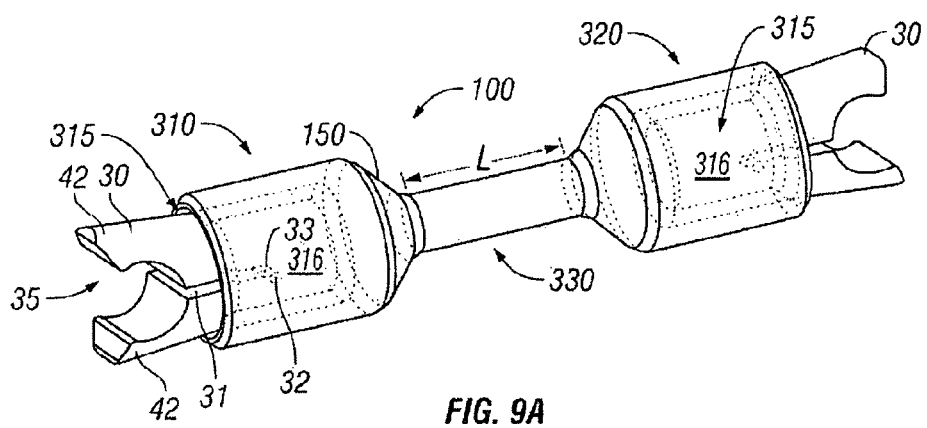
FIGS. 9A and 9B depict perspective and side views of one embodiment of a connector.
Figure 9B:
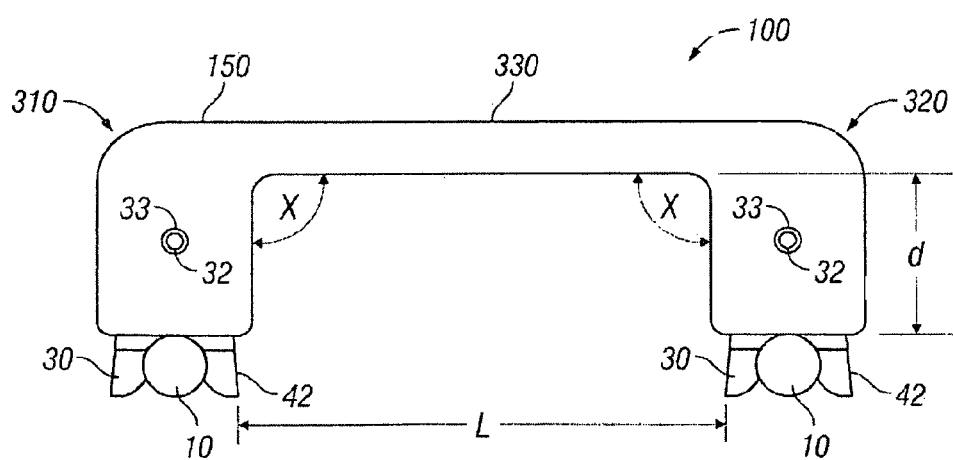

FIGS. 9A and 9B depict perspective and side views of embodiments of transverse member 150 having first end 310, second end 320 and central portion 330. In some embodiments, transverse member 150 depicted in FIGS. 9A and 9B may accommodate resilient insert 30 depicted in FIGS. 2A and 2B. Each of first end 310 and second end 320 may include cavity 315 for receiving resilient insert 30. In some embodiments, cavity 315 may have inner surface 316 textured or smooth for contact with resilient insert 30.

In some embodiments, transverse member 150 may have first end 310 and second end 320 joined by central portion 330 having length L. FIG. 9A depicts a perspective view of one embodiment of transverse member 150 in which first end 310, second end 320 and central portion 330 are substantially aligned with the longitudinal axis of transverse member 150.

Referring to FIG. 9B, connector 100 may have transverse member 150 having first end 310 and second end 320 angled relative to central portion 330. In some embodiments, the angle X of first end 310 or second end 320 relative to central portion 330 may be approximately 0 degrees. In some embodiments, the angle X of first end 310 or second end 320 relative to central portion 330 may be approximately 90 degrees. In some embodiments, the angle X of first end 310 or second end 320 relative to central portion 330 may be approximately 135 degrees.

In some embodiments, a set of connectors 100 may include transverse members 150 having various lengths and having first end 310 or second end 320 at various angles relative to central portion 330. In some embodiments, an instrumentation set may include connectors 100 having larger central portions 330 and a shorter first end 310 or second end 320. In FIG. 9A, connector 100 is depicted having a short central portion 330 that is substantially in line with the longitudinal axes of first end 310 and second end 320. In FIG. 9A, connector 100 is depicted having a long central portion 330 that is oriented approximately 90 degrees relative to first end 310 and second end 320.

In some embodiments, transverse member 150 may have an adjustable length. In some embodiments, central portion 330 of transverse member 150 may have an adjustable length. In some embodiments, an instrumentation set may include transverse members 150 having small central portions 330 and a longer first end 310 or second end 320. In some embodiments, an instrumentation set may include transverse members 150 having first end 310 and second end 320 in alignment with central portion 330 and transverse members 150 having first end 310 and second end 320 at some angle relative the longitudinal axis of central portion 330. Embodiments disclosed herein may make use of transverse members 150 having different lengths of central portion 330 and different angles of first end 310 and second end 320 to accommodate portions of the spine. For example, it may be desirable to connect two rods 10 and ensure connector 100 does not interfere with the spinous processes of vertebrae. A surgeon may select transverse member 150 with first end 310 and second end 320 at approximately 90 degrees to central portion 330 to circumvent the spinous process. The surgeon may also select transverse member 150 with first end 310 and second end 320 aligned with the longitudinal axis of central portion 330 to pass under the spinous process. Organs, tissues, muscles, bones or other tissues may be accommodated as well by selecting transverse member 150 having central portion 330 and first end 310 and second end 320 at some angle relative to central portion 330.

In some embodiments, connector 100 may include pin 32 and opening 33 for ensuring resilient insert 30 is retained in first end 310 or second end 320. In some embodiments, transverse member 150 may include a groove (not shown) in which pin 32 may be seated. In some embodiments, transverse member 150 may have resilient inserts 30 positioned in first end 310 or second end 320 and provisionally retained by pin 32 in opening 33 or a groove.

Figure 10:
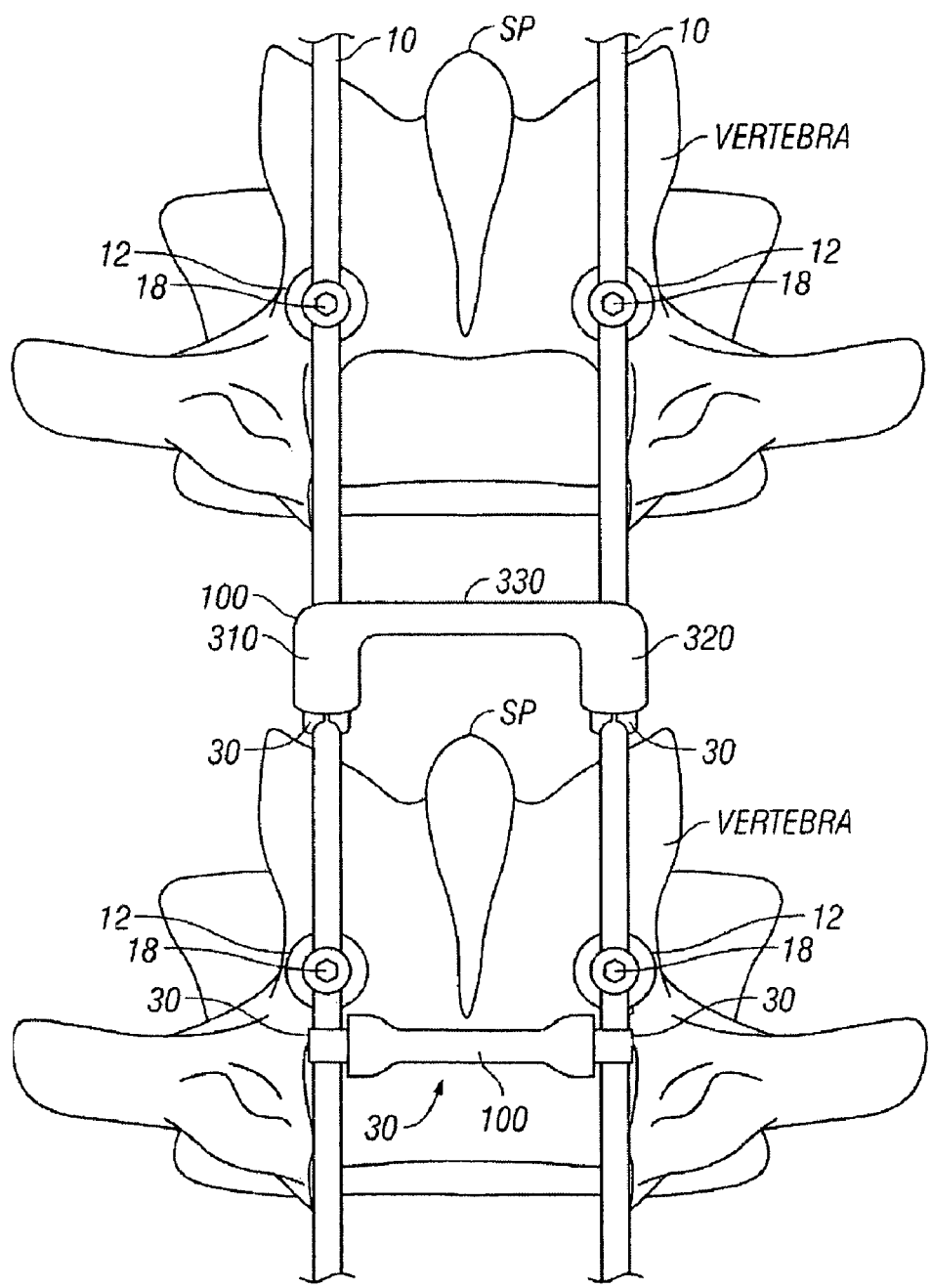
FIG. 10 depicts a posterior view of one embodiment of a portion of a spine stabilization system.

FIG. 10 depicts a posterior view of one embodiment of a multi-level spine stabilization system with rods 10 coupled to two connectors 100. Embodiments disclosed herein may be useful for coupling rods 10 located contralaterally on the spine. In some embodiments, a spine stabilization system may include bone fasteners 12 anchored in bone. Rod 10 may be coupled to bone fastener 12 using rod fastener 18. Connector 100 may be inserted into the patient and coupled to rods 10. Coupling rods 10 using connector 100 may provide additional rigidity or support for the spine stabilization system. Connector 100 may be inserted into the patient and coupled to rods 10. Coupling rods 10 using connector 100 may provide additional rigidity or support for the spine stabilization system.

As depicted in FIG. 10, in some embodiments, connectors may be positioned near bone fastener assemblies 12, spinous processes, or other components of a spine stabilization system or portions of the spine. In some embodiments, connector 100 may be positioned to circumvent a spinous process, avoid contact with the dural region of the spine, or the like. In some embodiments, connector 100 positioned near bone fastener assemblies 12 may provide additional support at the vertebra. In some embodiments, connector 100 positioned near a spinous process may distribute forces normally exerted on the vertebra. In some embodiments, connector 100 positioned near a spinous process may circumvent the spinous process to reduce forces on the spinous process. In some embodiments, connector 100 may be positioned during a MIS procedure. In some embodiments, connector 100 may be positioned during an invasive surgery.

Various instruments may be used in a minimally invasive procedure to form a spinal stabilization system in a patient. The instruments may include, but are not limited to, positioning needles, guide wires, dilators, bone awls, bone taps, dilators, drivers, tissue wedges, elongated member length estimating tools, mallets, tissue retractors, and tissue dilators. The instruments may not include torque wrenches or countertorque wrenches. An advantage of embodiments disclosed herein is that two rods 10 may be joined or cross-linked by connector 100 without requiring torques. Embodiments disclosed herein may stabilize a portion of the spine without applying torque to the spine. Torques applied to the spine may damage the vertebrae, cause pain or soreness to the patient, delay healing, or the like. Embodiments disclosed herein may be implanted without requiring countertorques. Eliminating countertorques may reduce the number of tools needed during surgery, reduce the complexity of the surgery, may reduce the number of hands needed for implanting a spine stabilization, or other benefits. The instruments may be provided in an instrumentation set. The instrumentation set may also include components of the spinal stabilization system. The components of the spinal stabilization system may include, but are not limited to, bone fastener assemblies of various sizes and/or lengths, rods, and inserts.

Instruments used to install a spine stabilization system may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

Dilators may be used during a minimally invasive surgical procedure to push aside tissue and create space to access components of a spinal stabilization system. In some embodiments, four tissue dilators of increasing diameter may be used to establish sufficient working space to accommodate instruments, connectors 100 and other spine stabilization system components. In some embodiments, especially for a mid-vertebra or for mid-vertebrae of a multi-level stabilization system, only three dilators may be needed to form sufficient working space. Dilators in an instrumentation set may increase in diameter incrementally by a selected amount. For example, outside diameters of dilators in an instrumentation set may increase sequentially by increments of about 0.5 mm.

In some embodiments, bone fasteners may be advanced into vertebrae on both sides of the spine in a patient. Collars may be coupled to the anchored bone fasteners. Rods 10 may be coupled to the collars to stabilize movement between two or more vertebrae on both sides of the spine. Sleeves may attach to resilient inserts 30. The sleeves may be used by a surgeon to advance resilient inserts 30 into the patient and to position resilient inserts 30 on both rods 10. Movement of the sleeves may alter an orientation of resilient inserts 30 relative to rod 10 of a spine stabilization system.

In some embodiments, a sleeve may be used as a retractor during a spinal stabilization procedure. Instruments may be inserted into sleeves in the dilators to position cylindrical bodies 20 on resilient inserts 30. Instruments may be inserted into sleeves in the dilators to position resilient inserts 30 in cylindrical bodies 20. Instruments may be inserted into sleeves in the dilators to advance resilient inserts 30 in cylindrical bodies.

A sleeve for a vertebral stabilization system may include one or more channels in a wall of the sleeve to allow access to rods 10 or vertebrae. For some spine stabilization procedures, only single-channel sleeves (i.e., sleeves with a single channel in a wall of the sleeve) may be used. For other spine stabilization procedures, one or more multi-channel sleeves (i.e., sleeves with two or more channels in a wall of the sleeve) may be used. Channels may provide flexibility to or enhance flexibility of a multi-channel sleeve. In some embodiments, a proximal portion of a multi-channel sleeve may have a solid circumference. A region of solid circumference in a multi-channel sleeve may enhance stability of the multi-channel sleeve. In some embodiments, a multi-channel sleeve may be longer than a single-channel sleeve.

A sleeve used in a spine stabilization procedure may be a multi-channel sleeve. Channels in a multi-channel sleeve may allow access to rods, resilient inserts, cylindrical bodies, or other spine stabilization components located ipsilateral and other rods, resilient inserts, cylindrical bodies, or other spine stabilization components located contralateral. In some embodiments, a sleeve may be advanced near a rod coupled to the spine. In some embodiments, a sleeve may be connected to a rod during surgery. In some embodiments, a sleeve may be connected to a collar coupled to a bone fastener during surgery. In some embodiments, a sleeve may be connected to a bone fastener during surgery. In some embodiments, a sleeve may be connected to resilient insert 30 such that positioning resilient insert 30 on rod 10 connects the sleeve to rod 10. In some embodiments, the sleeve may be connected to rod 10, the bone fastener or the collar, or be positioned near rod 10 and resilient insert 30 may be advanced down the sleeve for positioning on rod 10.

A channel in a wall of a sleeve may allow access to a vertebra on the ipsilateral or contralateral side of the spine that is to be stabilized with rod 10. In some embodiments, a single-channel sleeve may be used for access to a first resilient insert 30 for positioning on a first portion of rod 10. The single-channel sleeve may allow access to resilient insert 30, first rod 10 and/or second rod 10. In some embodiments, a multi-channel sleeve may be coupled to resilient insert 30. The multi-channel sleeve may allow access to resilient insert 30, first rod 10 and/or second rod 10.

Instruments may access a spine stabilization system through a passage in a sleeve. In some embodiments, a channel in a wall of a sleeve may extend a full length of the sleeve. In some embodiments, especially in embodiments of multi-channel sleeves, a channel in a wall of a sleeve may extend only a portion of the length of the sleeve. In some embodiments, a channel in a wall of a sleeve may extend 25%, 50%, 75%, 80%, 90%, 95% or more of the length of the sleeve. A channel may extend to a distal end of a sleeve such that resilient insert 30 may be inserted in the channel and be advanced from the sleeve and positioned onto rod 10 anchored to the spine. A channel may extend to a distal end of a sleeve such that connector 100 or components of connector 100, such as a cylindrical body 20, plate 90, or transverse member 150 inserted in the channel may pass from the sleeve onto resilient insert 30 positioned on rod 10.

A channel in a sleeve may be any of a variety of shapes. A cross-section shape may be circular, oval, or otherwise curved, or may be rectangular, square, or otherwise angular. A channel may have a width that exceeds a width of a connector, resilient insert, rod or other component that is to be inserted in the channel. In some embodiments, a channel may be a linear opening parallel to a longitudinal axis of the sleeve. In some embodiments, a channel may have a non-linear shape including, but not limited to, a helical pattern, an arc, an "L" shape, or an "S" shape. A non-linear channel may allow a component to travel along a predetermined path.

In some embodiments, a sleeve may have walls forming a passage, and channels that extend from a distal end of the sleeve through a portion of the walls. Channels in the walls may allow instruments to be positioned and used to form a plane through soft tissue. Connector 100 may be advanced into the patient to span between rods 10 anchored to vertebrae. A distal end of a sleeve may be tapered to reduce bulk (e.g., reduce diameter) at a surgical site.

In some embodiments, a sleeve may be coupled to resilient insert 30 positioned on rod 10. Instruments may be inserted through a passage in the sleeve to access rod 10 positioned in resilient insert 30. An instrument may be moved through a channel toward a contralateral vertebra to form a tissue plane in soft tissue between the sleeve and the contralateral vertebra.

A sleeve may be coupled to embodiments of resilient insert 30 during insertion and positioning of the resilient insert. A system having a sleeve coupled to resilient insert 30 should be simple, inexpensive to implement, and should not significantly weaken the mechanical strength of the resilient insert 30. Sleeves may be coupled to resilient inserts 30 using various coupling systems including, but not limited to, hooks, clamps, interlocking connection systems, and/or interference fits. In one embodiment of an interlocking connection system, a sleeve may include an opposing pair of deflectable arms. The deflectable arms may be forced outwards during coupling of resilient insert 30 to the sleeve. When resilient insert 30 is coupled to the sleeve, the deflectable arms may be positioned around resilient insert 30 to resist removal of the resilient insert. The presence of the deflectable arms around resilient insert 30 may inhibit rotation and translation of the sleeve relative to the resilient insert 30. Separation of the sleeve from the resilient insert may be achieved by insertion of an expander in the sleeve. The expander may be used to force the deflectable arms outwards and allow resilient insert 30 to be withdrawn from the sleeve.

In some embodiments, a distal end of a sleeve may be roughened or textured to frictionally engage a proximal surface of resilient insert 30. The frictional engagement may inhibit rotation of the sleeve relative to resilient insert 30. In some embodiments, a sleeve may include a pair of hinged arms configured to couple to resilient insert 30. The arms may be pivotally coupled together by a hinge located near a proximal end of a sleeve. In some sleeve embodiments, a sleeve may include a locking element or a biasing element (e.g., a spring) near or at the hinge. A locking element or biasing element may cause a clamping force to be exerted on the resilient insert to maintain resilient insert 30 in the sleeve and/or to inhibit rotation of resilient insert 30 in the sleeve.

In some sleeve embodiments, proximal portions of sleeves may be chamfered to allow ends of the sleeves to more closely approach each other than sleeves with a uniform cross section. Chamfered surfaces may reduce space between proximal ends of two sleeves. During some surgical procedures, only one of the sleeves may be chamfered. During some surgical procedures, the use of a sleeve with a chamfered surface may allow for a smaller incision than required when using non-chamfered sleeves. In some embodiments, other types of sleeves may be used to reduce space between proximal ends of sleeves. Other types of sleeves may include, but are not limited to, sleeves of different lengths, sleeves of different diameters, and sleeves with flexible end portions.

Sleeves may be of various lengths. Sleeves of different lengths may be used in the same surgical procedure. A sleeve length used in a spinal stabilization procedure may be determined by a patient's anatomy. Sleeves may be just short enough to allow manipulation by a medical practitioner above an incision in a patient. In some embodiments, sleeves may be about 3.5 to about 11.5 cm long. For example, a single-channel sleeve may be about 10 cm long. In some embodiments, sleeves may be about 11.5 cm to about 14 cm long. For example, a single-channel or a multi-channel sleeve may be about 12.5 cm long. A multi-channel sleeve may be longer than a single-channel sleeve. In some embodiments, a multi-channel sleeve may be at least about 15 cm long. For example, a multi-channel sleeve may be about 16 cm long. Sleeves that are too long may require a longer incision and/or a larger tissue plane for insertion of a spinal stabilization system. Insertion of a resilient insert, a cylindrical body, or other components may be more difficult with sleeves that are longer than necessary. Sleeves with excess length may be bulky and hard to manipulate during a surgical procedure.

A sleeve may be flexible over its entire length or include a flexible portion near a proximal end of the sleeve. A flexible portion may allow positioning of a proximal portion of a sleeve in a desired location. A flexible portion may be produced from any of various materials including, but not limited to, a surgical grade plastic, rubber, or metal. A flexible portion may be formed of various elements, including, but not limited to, a tube, a channel, or a plurality of linked segments.

In some embodiments, when 10 rods are positioned to span vertebrae, resilient insert 30 may be advanced into the patient and positioned on rod 10. During surgery, resilient insert 30 attached to a sleeve may be advanced into a patient and positioned on rod 10. After resilient insert 30 is positioned on rod 10, the sleeve may be rotated about resilient insert 30 and oriented towards contralateral rod 10 that spans a portion of the spine. In some embodiments, channels of the sleeves may be aligned so that connector 100 may be advanced into the patient and positioned on rods 10.

During a minimally invasive surgical procedure, a plane may be created in tissue from a first rod 10 to a second rod 10. Connector 100 may be positioned in the plane created during the surgical procedure. In some embodiments, a tissue wedge may be used to form a plane in tissue between first rod 10 and second rod 10. A blade used in a wedge may be a double-wedged blade, may have a diamond-like shape, may have blunt edges to avoid severing tissue during use of the tissue wedge, or the like. The distal end of a blade may be rounded. A shape of the distal end may inhibit damage to tissue and may facilitate movement of the blade towards a target location during formation of a plane in tissue between vertebrae. In some tissue wedge embodiments, a tissue wedge may include a hook. A cutting edge in the hook may be used to sever portions of tissue (e.g., fascia) through which a blade cannot form a plane. A cutting edge may be oriented in the blade so that severing of tissue results when the tissue wedge is pulled away from the spine.

An estimating tool may be used to estimate a distance between rods 10 in a spine stabilization system. Rods 10 may be the same size or may have different sizes or dimensions. The distance estimated by an estimating tool may be used to determine a desired length of connector 100 to couple the rods. An estimating tool may be designed such that a maximum separation distance exceeds an expected distance between rods 100. Fully extended arms may be manually compressed and inserted into passages of sleeves coupled to rods 10.

An estimating tool may be advanced through sleeves or dilators toward rods 10. In some embodiments, an estimating tool may be advanced toward rods 10 until members of the estimating tool contact rods 10 or resilient inserts 30. With the estimating tool contacting rods 10 and/or resilient inserts 30 positioned on rods 10, an activator of the estimating tool may be engaged. Engaging an activator of an estimating tool may limit the biasing element such that the distance between the members of the estimating tool does not exceed the distance between rods 10. With the activator engaged and the distance between the members of the estimating tool fixed to indicate the distance between rods 10, the estimating tool may be moved upwards to remove the estimating tool from the patient. When the estimating tool is moved upwards, arms may compress to facilitate removal of the estimating tool from the sleeves.

Once removed from the sleeves, the biasing element may restore the distance between the members of the estimating tool to indicate the separation between rods 10. The distance between the members of the estimating tool may be used to estimate a length of connector 100 needed to couple the rods 10. The distance may be read using a scale provided in the instrumentation kit. In some embodiments, the scale may be indicia or etching on a surface of the instrumentation kit.

In some embodiments, an estimating tool may include a gage having arms for providing an estimate of the distance between sleeves. Thus, with the arms of the estimating tool positioned together, the gage may have or may be set to a zero reading. With the arms extended to meet resistance in the sleeves, the gage may provide an estimate of the distance between the sleeves. The distance between the sleeves may be used to estimate a length of connector 100 needed to couple rods 10.

In some embodiments, once first resilient insert 30 has been positioned on rod 10, other components of connector 100 may be advanced into the patient. In some embodiments, once first resilient insert 30 has been positioned on rod 10, cylindrical body 20 may be positioned over first resilient insert 30. In some embodiments, once first resilient insert 30 has been positioned on rod 10, plate 90 may be advanced into the patient and resilient insert 30 may be positioned in cavity 92. In some embodiments, plate 90 may be positioned anterior to rods 10. In some embodiments, plate 90 may be positioned posterior to rods 10. In some embodiments, once first resilient insert 30 has been positioned on rod 10, first end 310 of transverse member 150 may be positioned over resilient insert 30.

After connector 100 has been positioned and advanced onto first resilient insert 30 as desired, second resilient insert 30 may be positioned on second rod 10 and may be positioned in connector 100 for coupling rods 10. A tool may connect to resilient insert 30. Resilient insert 30 may be attached to a second sleeve. Resilient insert 30 may be advanced into the patient via a second dilator positioned near the second rod 10. Resilient insert 30 may be positioned on second rod 10. Connector 100 may be rotated about first rod 10 until second resilient insert 30 can be positioned in connector 100. First and second resilient inserts 30 may be advanced into connector 100.

In some embodiments, resilient inserts 30 may be compressed into cylindrical body 20. Cylindrical body 20 may be rotated through the tissue plane created by the wedge or scalpel. Resilient insert 30 positioned on second rod 10 may be rotated about second rod 10. Resilient insert 30 may be positioned in passage 21 of cylindrical body 20. Compression applied to both resilient inserts 30 may advance resilient inserts 30 into cylindrical body 20.

In some embodiments, resilient inserts 30 may be advanced into plate 90. In some embodiments, knob 47 may be passed through plate 90 via passage 21 to position resilient insert 30 in plate 90. In some embodiments, knob 47 on resilient inserts 30 may be pulled to advance resilient inserts 30 into plate 90.

In some embodiments, resilient inserts 30 may be advanced into transverse member 150 of connector 100 having first end 310, second end 320 and transverse portion 330. In some embodiments, first end 310 and second end 320 may be substantially aligned with the longitudinal axis of connector 100. First end 310 may be positioned on first resilient insert 30 and connector 100 may be rotated in the tissue plane until second resilient insert may be positioned in second end 320. Resilient inserts 30 may be compressed into first end 310 and/or second end 320. In some embodiments, first end 310 and second end 320 may be oriented at some angle relative to transverse portion 330. First end 310 may be positioned on first resilient insert 30 while second end 320 is positioned on second resilient insert 30. In some embodiments, resilient inserts 30 may be compressed into first end 310 and second end 320. In some embodiments, resilient insert 30 having shank 45 and knob 47 may be positioned in first end 310 and second end 320 and knob 47 may be pulled to advance resilient inserts 30 into first end 310

Minimally invasive procedures may involve locating a surgical site and a position for a single skin incision to access the surgical site. The incision may be located above and between (e.g., centrally between) vertebrae to be stabilized. An opening under the skin may be enlarged to exceed the size of the skin incision. Movement and/or stretching of the incision and angulation of resilient inserts 30 about rods 10 may allow the length of the incision and/or the area of a tissue plane to be minimized. In some embodiments, minimally invasive insertion of a spinal stabilization system may not be visualized. In some embodiments, insertion of a spinal stabilization system may be a top-loading, mini-opening, muscle-splitting technique.

In one embodiment of a spinal stabilization system insertion method, the patient may be placed in a prone position on a radiolucent table with clearance available for a C-arm of a fluoroscope. For example, a Jackson table with a radiolucent Wilson frame attachment may be used. The ability to obtain high quality images is very important. Bolsters, frames, and pads may be inspected for radiolucency prior to the operation. Placing the patient in a knee-chest position (e.g., using an Andrews table) should be avoided. Care should be taken to avoid placing the patient's spine in kyphosis during positioning of the patient.

The C-arm of the fluoroscope should be able to freely rotate between the anteroposterior, lateral, and oblique positions for optimal visualization of patient anatomy during the procedure. The arm should be rotated through a full range of motion prior to beginning the procedure to ensure that there is no obstruction or radio-opaque object in the way. The fluoroscope may be positioned so that Ferguson views and "bullseye" views are obtainable. Once the patient is positioned and the ability to obtain fluoroscopic images of the target levels for instrumentation has been confirmed, the patient may be prepared and draped sterilely.

Various techniques may be used to plan the skin incisions and entry points. In one embodiment, the planning sequence for a single-level stabilization may include the following four steps. First, an anteroposterior image may be obtained with the spinous processes centered at the target vertebral levels. Vertical lines may be marked on the patient. Second, horizontal lines may be marked on the patient. In some embodiments, the lines may be drawn on the superior side of the center axes (superior to the mid-pedicle). Third, an oblique or "bullseye" view (i.e., down a longitudinal axis of a pedicle) may be obtained on each side of the patient. Vertical oblique view lines may be marked on the skin at the midpoints of each of the pedicles being stabilized. The oblique view lines may be drawn in a different color than the vertical lines drawn during the first step. Fourth, an incision may be made in the skin. The skin incision may be from about 2 cm to about 4 cm long. In some embodiments, the incision may be from about 2.5 cm to about 3 cm long. Limiting the length of the incision may enhance patient satisfaction with the procedure. The incisions may be pre-anesthetized with, for example, 1% lidocaine with 1:100,000 epinephrine. To blunt the pain response, a long spinal needle may be used to inject the planned muscle path in a retrograde fashion. Once the incision has been made, tissue surrounding the incision may be pulled and/or stretched to allow access to a target location.

After sterile preparation and draping, the entry points may be fluoroscopically rechecked. A scalpel may be used to make a stab wound. In one embodiment, the scalpel may be a #11 scalpel.

A guide wire may be used as a guide to position one or more successively sized dilators around a target location. A dilator may be a conduit with a regular shape (e.g., cylindrical) or an irregular shape (e.g., C-shaped). A dilator may form an opening through soft tissue to the pedicle. For patients with a thick fascia, it may be advantageous to make a nick in the fascia with a scalpel blade to facilitate passage of the dilators. The dilators may be passed sequentially over the guide wire. The dilators may be rotated during insertion to facilitate dilation of surrounding tissue. The dilators may be inserted until the leading edges contact the pedicle. A distal end of a dilator may be tapered to facilitate positioning of the dilator proximate the pedicle. An instrumentation set for a spinal stabilization system may include two, three, four, or more successively sized dilators.

As used herein, "an inner diameter just slightly larger than an outer diameter" may mean that the inner diameter is between about 0.03 mm and about 1.0 mm greater than the outer diameter. For example, an inner diameter of a first dilator may be about 0.5 mm greater than the outer diameter of the guide wire. Lengths of dilators in a successively sized set may decrease with increasing diameter to facilitate removal of the smaller dilators.

After tissue dilation has been achieved, a large diameter dilator may be used to guide a sleeve, a tool, resilient insert 30 and/or insertion instruments toward a target location.

In some embodiments, resilient insert 30 having channel 35 of an appropriate size or diameter may be selected for insertion in a patient. The size of channel 35 in resilient insert 30 may be verified with measurement indicia in an instrumentation set. In some embodiments, measurement indicia may be etched or printed on a portion of an instrumentation set. For example, the chosen resilient insert embodiment may be placed over the outline of a resilient insert 30 printed on a tray of the instrumentation set.

The chosen resilient insert 30 may be attached to a tool. The tool may advance resilient insert 30 through the dilator to rod 10. The tool may position resilient insert 30 on rod 10. The tool may provisionally lock resilient insert 30 to rod 10.

A plane of dilated tissue may be created between first rod 10 and second rod 10 to be stabilized with a spinal stabilization system. A first resilient insert 30 may be coupled to first rod 10. Second rod 10 may be ipsilateral to first rod 10. Second rod 10 may be contralateral to first rod 10. In one embodiment, a tissue wedge may be placed in the dilator such that the distal end of the tissue wedge contacts resilient insert 30. The proximal end of the dilator may be held such that tissue around the incision is not pulled or stretched. The tissue wedge may be wanded through the channel in the dilator toward the target location at the second rod 10, thereby creating a plane in muscle and other tissue between rods 10. In some embodiments, a tissue wedge may be pivoted about an inside proximal edge of the dilator such that the distal end of the tissue wedge bluntly splits the muscle and fascia along fibers and create a tissue plane between the two rods 10. The wanding action may be repeated more than once (e.g., two or three times) to create a good working plane and displace unwanted tissue from the plane. The wanding may create a tissue plane. In some embodiments, the tissue plane may be substantially trapezoidal.

A tissue plane may be made in a variety of shapes including, but not limited to, substantially trapezoidal, substantially rhomboidal, and substantially triangular. A tissue plane with a substantially geometric shape may have the basic geometric shape with, for example, slightly curved edges and/or slightly rounded corners or apices. In some embodiments, a dilator length may be chosen to reduce a size of a tissue plane that needs to be formed between rods 10. In some embodiments, creating a trapezoidal tissue plane may reduce the invasiveness of a procedure. Limiting the area of the plane may promote a faster recovery time and/or may reduce an amount of post-operative pain experienced by the patient.

In one embodiment, a tissue wedge may be coupled to a portion of a dilator to facilitate creation of a tissue plane. In one embodiment, two rods 10 may be targeted and resilient inserts 30 may be anchored to both rods 10 before creation of a tissue plane. A tissue wedge may be inserted at either of the rods 10. In some embodiments, the dilators may be coupled to each other at proximal ends of the dilators. The tissue wedge may be coupled to a dilator and the dilator may be used as an anchor during wanding. Other procedures may be used to create a tissue plane. For example, a tissue wedge may be worked downward from an incision to create a tissue plane. Alternatively, a scalpel may be used to cut from the surface of the body to vertebral bone. Extensive use of a scalpel, however, may remove benefits of a minimally invasive procedure.

With resilient inserts 30 positioned on rods 10, dilators may be oriented to facilitate insertion of other components of connector 100. In some embodiments, dilators may serve as tissue retractors during a spinal stabilization procedure. In some embodiments, channel openings in the dilators may face each other. In some embodiments, channel openings in the dilators may be angled relative to each other in various arrangements. A distance between the dilators may be estimated using an estimating tool. The distance between the dilators may be used to select a length of connector 100 needed to couple rods 10.

In one embodiment, flexible arms of an estimating tool may be positioned in dilators. With the activator disengaged, the estimating tool may be advanced toward the rods 10. The activator may be engaged. When the arms are withdrawn from the dilators, a biasing element may allow the arms to extend to the length indicative of the distance between rods 10. A length of connector 100 may be selected by measuring a distance between the members of the estimating tool. The measured distance may be increased by an amount. In one embodiment, about 5 mm to about 30 mm (e.g., about 15 mm) may be added to the measured distance.

In one embodiment, connector 100 of desired length may be chosen by estimating a distance between the dilators without the use of an estimating tool. The dilators may be positioned as desired (e.g., substantially parallel to each other). A distance between the most distant outer edges of the dilators may be estimated. The estimated distance may be adjusted by an amount to accommodate cylindrical body 20. The estimated distance may be adjusted by an amount to accommodate plate 90. The estimated distance may be adjusted by an amount to accommodate transverse member 150 having first end 310, second end 320 and transverse portion 330 substantially aligned. The estimated distance may be adjusted by an amount to accommodate transverse member 150 having first end 310 and second end 320 oriented at some angle relative to transverse portion 330.

Prior to insertion of connector 100, the tissue wedge or targeting needle may be used to wand between rods 10 to ensure a clean plane between rods 10. An end of connector 100 may be inserted at an angle or substantially longitudinally in a passage and/or channel of a dilator coupled to rod 10. Inserting connector 100 at an angle or substantially longitudinally allows the length of the incision and/or the area of the tissue plane to remain advantageously small. In some embodiments, dilators coupled to rods 10 may remain essentially unconstrained relative to each other during insertion of connector 100. In some embodiments, angular orientation of dilators, sleeves or resilient inserts 30 may determine a trajectory of the connector 100. Inserting connector 100 down two or more dilators and through an open path (i.e., the tissue plane) may allow a medical practitioner to avoid surgical difficulties associated with anatomical abnormalities and/or misalignment of system components (e.g., in multi-level stabilization procedures).

Insertion of connector 100 may not be visualized subcutaneously. Therefore, a positioning tool may be used to guide connector 100 down the dilators. A distal portion of the positioning tool may be contoured. The contour may allow for some rotation of connector 100. With slight pressure, connector 100 may be rotated subcutaneously into a substantially horizontal position. The positioning tool may be held firmly while still allowing a rocking movement between connector 100 and the distal end of the positioning tool. Movement of connector 100 may allow connector 100 to be maneuvered down the dilators.

In some embodiments, resilient insert 30 may be inserted into passage 21, cavity 92, first end 310 or second end 320 using a slight twisting to reduce friction or otherwise facilitate insertion. Slight twisting of resilient insert 30 may be enough to avoid static friction and the associated torque. An advantage to embodiments disclosed herein may be the absence or reduction of torques applied to spine stabilization system 100 (and the spine) during surgery. Torques applied to the spine can stress the injury, cause pain for the patient, slow the healing process, and other undesirable effects. A spine stabilization system that does not exert torque on the vertebrae may require fewer tools, may simplify the surgery, reduce surgery time, and other benefits.

In some embodiments, resilient inserts 30 may be advanced into cylindrical body 20 to couple rods 10. Pressure may be applied to a first resilient insert positioned in a first end 34 of connector 100. An opposing pressure may be applied to a second resilient insert 30 positioned contralaterally and oriented in an opposite direction. By applying equal and opposite pressures to resilient inserts 30, resilient inserts 30 may be advanced into cylindrical body 20 without torques or other undesirable forces on the patient.

In some embodiments, resilient inserts 30 may be advanced into plate 90 to couple rods 10. In some embodiments, plate 90 may be positioned anterior to rods 10. Pressure may be applied to rods 10 and an opposing pressure may be applied to plate 90. In some embodiments, a tool may be coupled to the edges of plate 90. By applying a downward pressure on rods 10 and an upward pressure on plate 90, resilient inserts 30 may be advanced into plate 90 without torque.

In some embodiments, resilient inserts 30 may be advanced into transverse member 150 having first end 310 and second end 320. In some embodiments, first end 310 and second end 320 may be aligned. Applying a pressure to resilient insert 30 in first end 310 may be opposed by applying a pressure to resilient insert 30 positioned in second end 320. In some embodiments, first end 310 and second end 320 may be oriented at some angle relative to central portion 330. Pressure may be applied to first end 310 and/or second end 320 and an opposing force may be applied to central portion 330 to advance resilient inserts 30 into first end 310 and second end 320.

In some embodiments, pin 32 may be inserted in cylindrical body 20 or transverse member 150 to retain resilient insert 30. In some embodiments, pin 32 may be inserted in opening 38. In some embodiments, pin 32 may be inserted in groove 34. In some embodiments, pin 32 may be inserted after cylindrical body 20 or transverse member 150 has been coupled to rods 10. After pin 32 is positioned in cylindrical body 20 or transverse member 150, the tool may be removed from the patient.

In some embodiments, after resilient insert 30 is seated on rod 10, the surgeon may seat other resilient inserts 30 on rod 10 before advancing resilient inserts 30 into connector 100. Seating multiple resilient inserts 30 on rod 10 before advancing any of the resilient inserts 30 allows a surgeon to verify placement or positioning of rod 10 and resilient inserts 30. The surgeon may remove rod 10 from channels 35, move rod 10, bend rod 10, or make other adjustments or changes to connector 100. Rod 10 may be positioned in a first resilient insert 30 and then second resilient insert 30.

In some embodiments, pin 32 may be removed from resilient insert 30 to allow a surgeon to remove resilient insert 30 from cylindrical body 20, plate 90 or transverse member 150. Resilient insert 30 may be removed from cylindrical body 20, plate 90 or transverse member 150 to allow access to rod 10. Rod 10 may be removed from resilient insert 30. When rod 10 is removed from resilient insert 30, a surgeon may access rod 10 and resilient insert 30.

Embodiments of connector 100 may be used to stabilize two or more vertebral levels (i.e., at least three adjacent vertebrae). In one embodiment, an incision may be made in the skin between the outermost vertebrae coupled to rods 10. A first connector 100 may be coupled to rods 10. The first connector may couple to rods 10 at a target location. A second connector may be coupled to rods 10 at a second location. A third connector 100 may be coupled to the rods 10 at a third location. A connector 100 may be used to couple rods 10 in the cervical portion of the spine, in the thoracic portion of the spine, and/or the lumbar portion of the spine. In one embodiment of a method for a two-level spinal stabilization procedure, an incision may be made above a target location. A first connector 100 may be coupled to rods 10. After the first connector 100 is secured, the spine may be prevented from movement.

In some embodiments, connectors 100 may be inserted using an invasive procedure. Since insertion of connectors 100 in an invasive procedure may be visualized, components and/or instruments (e.g., dilators) may not be needed for the invasive (i.e., open) procedure. Thus, resilient inserts 30, cylindrical bodies 20, plates 90, transverse members 150 used in an invasive procedure may differ from resilient inserts 30, cylindrical bodies 20, plates 90 or transverse members 150 used in a minimally invasive procedure.

In some embodiments, tools used in an invasive procedure may be similar to tools used in a minimally invasive procedure. In some embodiments, methods of installing connectors 100 in an invasive procedure may be similar to methods of installing connectors 100 in a minimally invasive procedure.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure. It is to be understood that the forms of the disclosure shown and described herein are to be taken as the presently preferred embodiments. Elements and materials may be substituted for those illustrated and described herein, parts and processes may be reversed, and certain features of the disclosure may be utilized independently, all as would be apparent to one skilled in the art after having the benefit of this description of the disclosure. Changes may be made in the elements described herein without departing from the spirit and scope of the disclosure as described in the following claims.

What is claimed is:

1. An apparatus for joining two rods, comprising:
a first resilient insert comprising:
  a first set of two deflectable arms; and
  a first channel formed between the first set of two deflectable arms, wherein the first channel has a width approximately equal to the diameter of a first spinal rod;
a second resilient insert comprising:
  a second set of two deflectable arms; and
  a second channel formed between the second set of two deflectable arms,
    wherein the second channel has a width approximately equal to the diameter of a second spinal rod,
    wherein the first spinal rod and the second spinal rod have similar or dissimilar diameter or shape; and
a body having a first opening at a first end, a second opening at a second end, and a passage in communication with the first opening and the second opening from the first end to the second end, wherein the first opening has an inner diameter, the second opening has an inner diameter, and the passage has an inner diameter,
  wherein the first resilient insert has a portion having an outer diameter greater than the inner diameter of the first opening of the body when the first resilient insert is in a neutral state,
  wherein advancement of the first resilient insert into the first opening of the body deflects the first set of two deflectable arms inward, causing the width of the first channel to decrease, thereby holding the first spinal rod at the first end of the body, and
  wherein the second resilient insert has a portion having an outer diameter greater than the inner diameter of the second opening of the body when the second resilient insert is in a neutral state,
  wherein advancement of the second resilient insert into the second opening of the body deflects the second set of two deflectable arms inward, causing the width of the second channel to decrease, thereby holding the second spinal rod at the second end of the body.

2. The apparatus of claim 1, wherein at least one of the first set of two deflectable arms and the second set of the two deflectable arms comprise beveled surfaces proximate the first channel or the second channel.

3. The apparatus of claim 1, wherein at least one of the first set of two deflectable arms and the second set of the two deflectable arms comprise radiused surfaces proximate the first channel or the second channel.

4. The apparatus of claim 1, wherein at least one of the first end and the second end of the body comprises two recessed portions, wherein each recessed portion has an associated width greater than the diameter of the first spinal rod or the second spinal rod.

5. The apparatus of claim 1, wherein the first channel in the first resilient insert comprises a first slot, wherein compression of the first slot deflects the first set of two deflectable arms inward to decrease the width of the first channel.

6. The apparatus of claim 1, wherein the second channel in the second resilient insert comprises a second slot, wherein compression of the second slot deflects the second set of two deflectable arms inward to decrease the width of the second channel.

7. The apparatus of claim 1, wherein at least one of the first resilient insert and the second resilient insert is cannulated.

8. The apparatus of claim 1, wherein at least one of the first set of two deflectable arms and the second set of two deflectable arms has a first width and a second width that is greater than the first width,
  wherein advancement of the first resilient insert into the first opening of the body comprises advancement of the first resilient insert until the first width thereof contacts interior walls of the first end of the body and the second width thereof is compressed against the interior walls of the first end of the body, and
  wherein advancement of the second resilient insert into the second opening of the body comprises advancement of the second resilient insert until the first width thereof contacts interior walls of the second end of the body and the second width thereof is compressed against the interior walls of the second end of the body.

9. The apparatus of claim 1, wherein at least one of the first resilient insert and the second resilient insert comprises a pin.

10. The apparatus of claim 9, wherein the body further comprises a groove and wherein the pin is configured to engage with the groove in the passage.

11. A system for stabilizing a portion of a spine, comprising:
a first spinal rod having a substantially circular cross-sectional geometry:
a second spinal rod having a substantially circular cross-sectional geometry,
  wherein the first spinal rod and the second spinal rod have similar or dissimilar diameter or shape; and
a spinal rod connector comprising:
  a first resilient insert comprising:
    a first set of two deflectable arms; and
    a first channel formed between the first set of two deflectable arms;
  a second resilient insert comprising:
    a second set of two deflectable arms; and
    a second channel formed between the second set of two deflectable arms; and
  a body having a first opening at a first end, a second opening at a second end, and a passage in communication with the first opening and the second opening from the first end to the second end, wherein the first opening has an inner diameter, the second opening has an inner diameter, and the passage has an inner diameter,
    wherein the first resilient insert has a portion having an outer diameter greater than the inner diameter of the first opening of the body when the first resilient insert is in a neutral state,
    wherein advancement of the first resilient insert into the first opening of the body deflects the first set of two deflectable arms inward, causing the width of the first channel to decrease, thereby holding the first spinal rod at the first end of the body, and
    wherein the second resilient insert has a portion having an outer diameter greater than the inner diameter of the second opening of the body when the second resilient insert is in a neutral state,
    wherein advancement of the second resilient insert into the second opening of the body deflects the second set of two deflectable arms inward, causing the width of the second channel to decrease, thereby holding the second spinal rod at the second end of the body.

12. The system of claim 11, wherein at least one of the first set of two deflectable arms and the second set of the two deflectable arms comprise beveled surfaces proximate the first channel or the second channel.

13. The system of claim 11, wherein at least one of the first set of two deflectable arms and the second set of the two deflectable arms comprise radiused surfaces proximate the first channel or the second channel.

14. The system of claim 11, wherein the second end of the cylindrical body comprises two recessed portions, wherein each recessed portion has an associated width greater than the diameter of the second spinal rod.

15. The system of claim 11, wherein the first channel in the first resilient insert comprises a first slot, wherein compression of the first slot deflects the first set of two deflectable arms inward to decrease the width of the first channel.

16. The system of claim 11, wherein the second channel in the second resilient insert comprises a second slot, wherein compression of the second slot deflects the second set of two deflectable arms inward to decrease the width of the second channel.

17. The system of claim 11, further comprising:
two or more bone fasteners, wherein each bone fastener comprises:
a threaded shank for advancement into a vertebral body; and
a head connected to the threaded shank, wherein coupling the first spinal rod or the second spinal rod to the head inhibits motion of the vertebral body relative to the first spinal rod or the second spinal rod.

18. The system of claim 11, wherein at least one of the first resilient insert and the second resilient insert comprises a pin.

19. The system of claim 18, wherein the body of the spinal rod connector further comprises a groove and wherein the pin is configured to engage with the groove in the passage.

* * * * *